(12) United States Patent
Eguchi et al.

(10) Patent No.: US 10,265,003 B2
(45) Date of Patent: Apr. 23, 2019

(54) BIOLOGICAL INFORMATION ACQUISITION DEVICE AND ELECTRONIC DEVICE

(71) Applicant: SEIKO EPSON CORPORATION, Tokyo (JP)

(72) Inventors: Tsukasa Eguchi, Nagano (JP); Hideto Ishiguro, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 698 days.

(21) Appl. No.: 14/818,605

(22) Filed: Aug. 5, 2015

(65) Prior Publication Data

US 2016/0058339 A1 Mar. 3, 2016

(30) Foreign Application Priority Data

Aug. 26, 2014 (JP) ................................. 2014-171264

(51) Int. Cl.
| | |
|---|---|
| *A61B 5/1455* | (2006.01) |
| *A61B 5/145* | (2006.01) |
| *A61B 5/00* | (2006.01) |
| *A61B 5/02* | (2006.01) |
| *H01L 51/00* | (2006.01) |

(52) U.S. Cl.
CPC ........ *A61B 5/1455* (2013.01); *A61B 5/14532* (2013.01); *A61B 5/14546* (2013.01); *A61B 5/489* (2013.01); *A61B 5/02007* (2013.01); *A61B 5/681* (2013.01); *H01L 51/006* (2013.01); *H01L 51/0069* (2013.01)

(58) Field of Classification Search
CPC .............. A61B 5/1455; A61B 5/14532; A61B 5/14546; A61B 5/489
See application file for complete search history.

(56) References Cited

U.S. PATENT DOCUMENTS

| | | | |
|---|---|---|---|
| 5,974,338 A | 10/1999 | Asano et al. | |
| 6,104,938 A | 8/2000 | Huiku et al. | |
| 8,352,003 B2* | 1/2013 | Sawada | A61B 5/0261 600/310 |
| 8,467,855 B2 | 6/2013 | Yasui | |
| 8,649,836 B2* | 2/2014 | Shimizu | A61B 5/14532 600/310 |

(Continued)

FOREIGN PATENT DOCUMENTS

| | | |
|---|---|---|
| JP | 11-000323 A | 1/1999 |
| JP | 4072240 B2 | 4/2008 |

(Continued)

OTHER PUBLICATIONS

The Extended European Search Report for the corresponding European Application No. 15182147.7 dated Jan. 20, 2016.

*Primary Examiner* — Eric F Winakur

(57) ABSTRACT

A small biological information acquisition device that can noninvasively acquire biological information is provided. The biological information acquisition device includes a first light emitting element 30A serving as a first infrared light source that is used for acquiring positional information of blood vessels and emits infrared light having a peak wavelength λ1, and a second light emitting element 30B serving as a second infrared light source that is used for spectral analysis and emits infrared light having a peak wavelength λ2 different from the peak wavelength λ1.

15 Claims, 12 Drawing Sheets

(56) References Cited

U.S. PATENT DOCUMENTS

| | | | |
|---|---|---|---|
| 8,818,473 B2 * | 8/2014 | McKenna | A61B 5/14551 600/310 |
| 2011/0205535 A1 | 8/2011 | Soller et al. | |
| 2014/0018645 A1 | 1/2014 | Wada et al. | |
| 2014/0024904 A1 | 1/2014 | Takinami | |

FOREIGN PATENT DOCUMENTS

| | | |
|---|---|---|
| JP | 2009-119173 A | 6/2009 |
| JP | 4331959 B2 | 9/2009 |
| JP | 4517004 B2 | 8/2010 |
| JP | 2011-149901 A | 8/2011 |
| JP | 2012-217554 A | 11/2012 |
| JP | 2012-217570 A | 11/2012 |
| JP | 2012-218480 A | 11/2012 |

\* cited by examiner

BIOLOGICAL INFORMATION ACQUISITION DEVICE AND ELECTRONIC DEVICE

BACKGROUND

1. Technical Field

The present invention relates to a biological information acquisition device and an electronic device.

2. Related Art

As a biological information acquisition device, JP-A-11-323 discloses a noninvasive blood analyzer capable of irradiating a living body with light (infrared light) having a wavelength of 600 to 900 nm that is not greatly absorbed by water and can pass through biological tissues and analyzing a specific component in blood, such as a hemoglobin concentration or a hematocrit, for example. JP-A-2009-119173 discloses an optical scanning measurement device that can irradiate and scan an eyeground with visible light and infrared light and acquire images of blood vessels in the eyeground and content information of a specific component, such as glucose or hemoglobin, in blood in the blood vessels. This optical scanning measurement device may emit infrared light having a plurality of wavelengths or may vary the wavelength of infrared light to be emitted.

However, there is a problem with the noninvasive blood analyzer of JP-A-11-323 in that it is difficult to determine the positions of blood vessels to perform blood analysis. Also, there is a problem with the optical scanning measurement device of JP-A-2009-119173 in that the mechanism for scanning an eyeground using visible light and infrared light is complicated, thus making it difficult to reduce the size of the device.

SUMMARY

An advantage of some aspects of the invention can be realized as the following embodiments or application examples.

An application example is directed to a biological information acquisition device including a first infrared light source that emits infrared light having a peak wavelength $\lambda 1$, and a second infrared light source that emits infrared light having a peak wavelength $\lambda 2$ different from the peak wavelength $\lambda 1$.

With this application example, a biological information acquisition device can be provided that can noninvasively acquire positional information of blood vessels in a living body and analysis information of the amount of a specific component contained in blood in the blood vessels and the like.

In the biological information acquisition device according to the application example, the peak wavelength $\lambda 1$ is in a range of greater than 700 nm to 900 nm or less.

With this configuration, the peak wavelength $\lambda 1$ is in a wavelength range in which light is more greatly absorbed by a blood component such as hemoglobin than by the surrounding tissues, thus making it possible to determine the positions of blood vessels in a living body.

In the biological information acquisition device according to the application example, the peak wavelength $\lambda 2$ is in a range of greater than 900 nm to 2000 nm or less.

With this configuration, the peak wavelength $\lambda 2$ is in a wavelength range in which light is absorbed by a blood component such as glucose, thus making it possible to determine a blood sugar level by detecting the content of glucose, for example.

In the biological information acquisition device according to the application example, it is preferable that the first infrared light source and the second infrared light source are disposed on the same surface.

With this configuration, a small biological information acquisition device can be realized.

In the biological information acquisition device according to the application example, it is preferable that a plurality of the first infrared light sources and a plurality of the second infrared light sources are disposed on the same surface, and the second infrared light sources are larger in number than the first infrared light sources.

With this configuration, positional information of blood vessels, that is, images of blood vessels, in a predetermined range can be acquired by disposing a plurality of first infrared light sources. In addition, the amount of light to be used in spectroscopic analysis can be ensured and the analysis can be performed with favorable detection accuracy by providing a larger number of second infrared light sources than the number of first infrared light sources.

In the biological information acquisition device according to the application example, a plurality of the first infrared light sources may be disposed on the same surface, and the second infrared light source may be disposed around the surface.

With this configuration, compared with the case where the first infrared light sources and the second infrared light sources are disposed on the same surface, the amount of infrared light emitted by the first infrared light sources can be ensured to acquire clear images of blood vessels, and the substantial range irradiated with infrared light emitted by the first infrared light sources can be enlarged.

In the biological information acquisition device according to the application example, a plurality of the second infrared light sources may be disposed around the surface, and the plurality of second infrared light sources may include second infrared light sources having peak wavelengths $\lambda 2$ of different values.

With this configuration, a plurality of peak wavelengths $\lambda 2$ of infrared light emitted by the plurality of second infrared light sources can be set corresponding to the wavelengths of light to be absorbed by the blood components to be analyzed.

In the biological information acquisition device according to the application example, it is preferable that the second infrared light sources are LED elements.

With this configuration, a small biological information acquisition device having a high-performance analytical function can be realized because LED elements are small point light sources and can emit light having a stable peak wavelength.

In the biological information acquisition device according to the application example, a plurality of the second infrared light sources may be disposed on the same surface, and the first infrared light source may be disposed around the surface.

With this configuration, compared with the case where the first infrared light sources and the second infrared light sources are disposed on the same surface, the amount of infrared light emitted by the second infrared light sources can be ensured to analyze blood components with high detection accuracy, and a substantial range irradiated with infrared light emitted by the second infrared light sources can be enlarged.

The biological information acquisition device according to the application example includes a light receiving portion disposed on a side opposite to a direction in which infrared light is emitted by the first infrared light source or the second infrared light source.

With this configuration, a living body is irradiated with infrared light emitted by the first infrared light source, and the infrared light reflected by the living body is received by the light receiving portion, as a result of which image information of blood vessels can be acquired. In addition, a living body is irradiated with infrared light emitted by the second infrared light source, and the infrared light reflected by the living body is received by the light receiving portion, as a result of which information of a specific component contained in blood in the blood vessels can be acquired.

In the biological information acquisition device according to the application example, at least one of the first infrared light source and the second infrared light source is an organic electroluminescent element.

In this configuration, the organic electroluminescent elements are thinner and have a higher degree of design freedom in shape and arrangement than LED elements or the like. Accordingly, if the first infrared light source is configured by the organic electroluminescent element, high-definition images of blood vessels can be acquired. In addition, if the second infrared light source is configured by the organic electroluminescent element, a surface light source for spectroscopic analysis in which light emission unevenness is less conspicuous can be realized. That is, a thin high-performance biological information acquisition device can be realized.

It is preferable that the biological information acquisition device according to the application example includes a variable band pass filter capable of changing a spectral distribution of infrared light that is incident on the light receiving portion.

With this configuration, the variable band pass filter can be controlled such that infrared light in a desired wavelength range is selectively incident on the light receiving portion. In addition, noise in the acquisition of images of blood vessels and the analysis of a specific component contained in blood can be reduced by controlling the variable band pass filter such that infrared light out of the desired wavelength range is not incident on the light receiving portion.

In the biological information acquisition device according to the application example, the variable band pass filter is controlled such that infrared light having the peak wavelength λ1 and infrared light having the peak wavelength λ2 are incident on the light receiving portion in different time periods.

With this configuration, the acquisition of images of blood vessels and the spectroscopic analysis of a specific component in blood in the blood vessels can be reliably performed separately by controlling the variable band pass filter.

In the biological information acquisition device according to the application example, the second infrared light source is a wide-band infrared light source that emits light having a wavelength of 900 nm or more to 2000 nm or less, and the variable band pass filter is controlled such that infrared light having peak wavelengths λ2 of different values is incident on the light receiving portion in different time periods.

With this configuration, infrared light in a desired wavelength range included in a wavelength range of 900 nm or more to 2000 nm or less can be allowed to be selectively incident on the light receiving portion.

Another application example is directed to an electronic device including the biological information acquisition device according to the above-described application example.

With this application example, an electronic device can be provided that can acquire positional information of blood vessels in a living body and information of the amount of a specific component contained in blood in the blood vessels and the like in a noncontact manner and that can be useful in health care and medical treatment, for example.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes embodiments in which the invention is embodied, with reference to the drawings. It should be noted that the diagrams to be used are magnified or reduced as appropriate such that portions to be described can be recognized.

First Embodiment

Electronic Device

Figure 1:
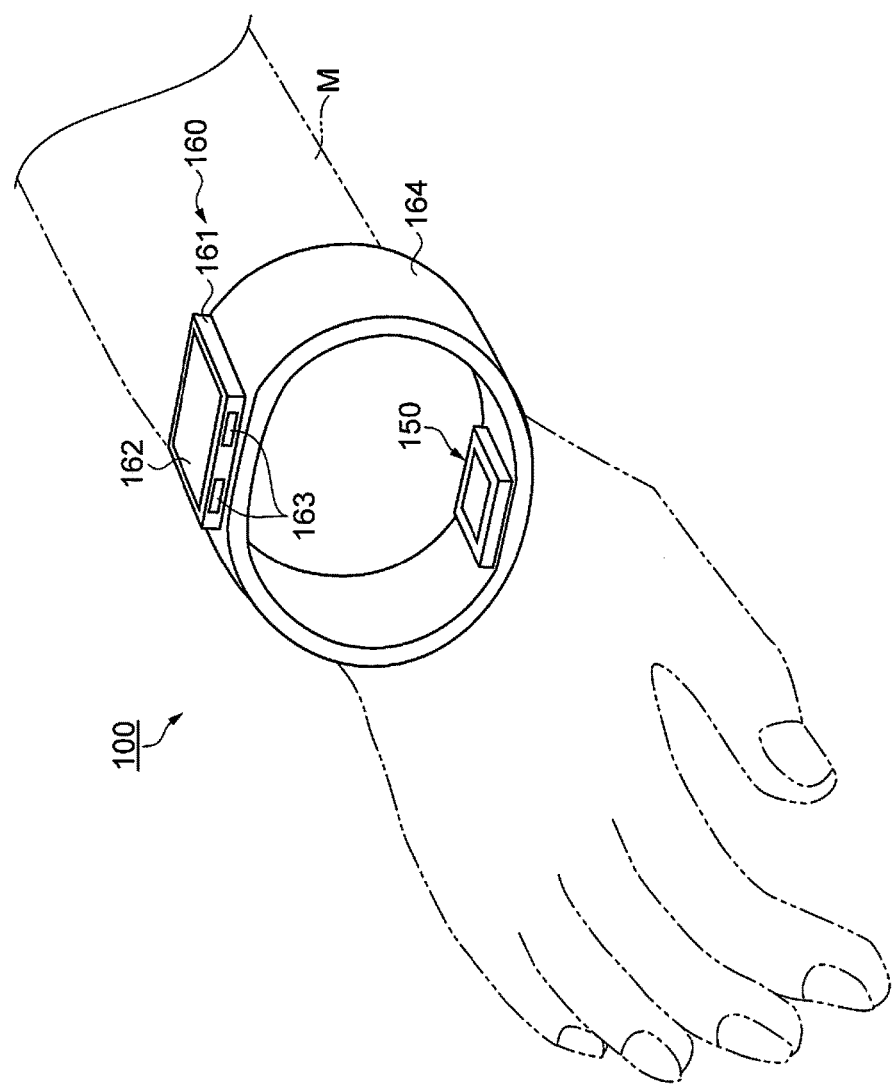
FIG. 1 is a perspective view illustrating a configuration of a portable information terminal.
Figure 2:
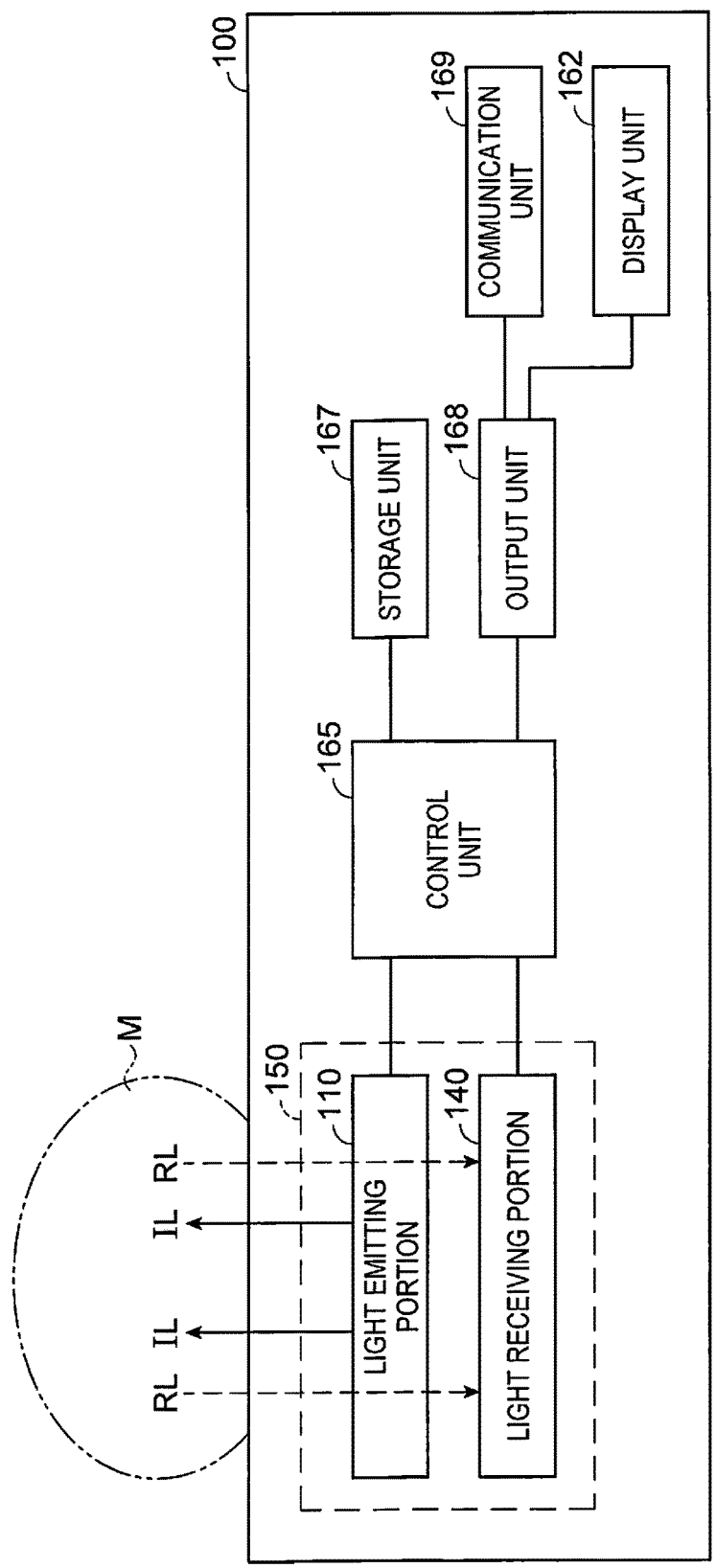
FIG. 2 is a block diagram illustrating an electrical configuration of the portable information terminal.

First, a portable information terminal will be taken as an example of an electronic device according to this embodiment and described with reference to FIGS. 1 and 2. FIG. 1 is a perspective view illustrating a configuration of a portable information terminal, and FIG. 2 is a block diagram illustrating an electrical configuration of the portable information terminal.

As shown in FIG. 1, a portable information terminal 100 according to this embodiment is a device that can be worn around a wrist of a human body M to acquire images of blood vessels inside the wrist, information of a specific component in blood in the blood vessels, and the like. The portable information terminal 100 includes an annular belt 164 that can be worn around a wrist, a main body portion 160 attached to the outer side of the belt 164, and a sensor unit 150 attached to the inner side of the belt 164 at a position opposed to the main body portion 160. The main body portion 160 includes a main body case 161, and a display unit 162 incorporated in the main body case 161. In addition to the display unit 162, an operation button 163, a circuit system (see FIG. 2) such as a control unit 165, which will be described later, a battery serving as a power source, and the like are incorporated in the main body case 161.

The sensor unit 150 is an example of the biological information acquisition device according to an aspect of the invention, and is electrically connected to the main body portion 160 by a wire (not shown in FIG. 1) incorporated in the belt 164.

The portable information terminal 100 is used by being worn around a wrist such that the sensor unit 150 comes into contact with the wrist on a palm side, which is a side opposite to the back of the hand. When the portable information terminal 100 is worn in this manner, it is possible to avoid variation in the detection sensitivity of the sensor unit 150 due to the color of the skin.

It should be noted that although the portable information terminal 100 according to this embodiment has a configuration in which the main body portion 160 and the sensor unit 150 are separately attached to the belt 164, a configuration may be adopted in which the main body portion 160 and the sensor unit 150 are integrated and attached to the belt 164.

As shown in FIG. 2, the portable information terminal 100 includes a control unit 165, and a sensor unit 150, a storage unit 167 and an output unit 168 that are electrically connected to the control unit 165. Also, the portable information terminal 100 includes a display unit 162 and a communication unit 169 that are electrically connected to the output unit 168.

The sensor unit 150 includes a light emitting portion 110 and a light receiving portion 140. The light emitting portion 110 and the light receiving portion 140 are electrically connected to the control unit 165. The light emitting portion 110 includes a light source portion that emits infrared light IL having a wavelength in a range of 700 to 2000 nm. The control unit 165 drives the light emitting portion 110 to emit infrared light IL having a desired peak wavelength. The infrared light IL propagates into the human body M and scatters. A configuration is adopted in which a portion of the infrared light IL scattering inside the human body M can be received by the light receiving portion 140 as reflected light RL.

The control unit 165 can store information of the reflected light RL received by the light receiving portion 140 in the storage unit 167. In addition, the control unit 165 causes the output unit 168 to process the information of the reflected light RL. The output unit 168 converts the information of the reflected light RL into image information of blood vessels and outputs the image information, and converts the information of the reflected light RL into content information of a specific component in blood and outputs the content information. In addition, the control unit 165 can display the converted image information of blood vessels and the converted information of the specific component in blood on the display unit 162. Furthermore, the information can be transmitted from the communication unit 169 to another information processing device. The communication unit 169 may be a wired communication means that is connected to another information processing device by a cable or a wireless communication means such as Bluetooth (registered trademark). It should be noted that the control unit 165 may display not only the obtained information related to blood vessels and blood but also information of a program stored in the storage unit 167 in advance, a current time, and the like on the display unit 162.

Biological Information Acquisition Device

Figure 3:
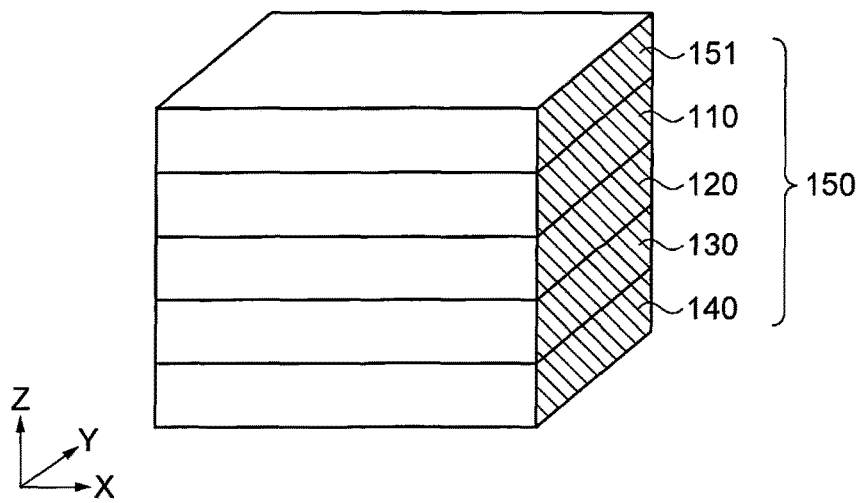
FIG. 3 is a schematic perspective view illustrating a configuration of a sensor unit.

Next, the sensor unit 150 serving as the biological information acquisition device according to this embodiment will be described with reference to FIGS. 3 and 4. FIG. 3 is a schematic perspective view illustrating a configuration of a sensor unit, and FIG. 4 is a schematic cross-sectional view illustrating a structure of the sensor unit.

As shown in FIG. 3, the sensor unit 150 includes a protective portion 151, the light emitting portion 110, a variable spectral portion 120, a light blocking portion 130, and a light receiving portion 140. Each portion has a plate shape, and a configuration is adopted in which the light blocking portion 130, the variable spectral portion 120, the light emitting portion 110, and the protective portion 151 are stacked on the light receiving portion 140 in the stated order. It should be noted that the sensor unit 150 includes a case (not shown) that accommodates the stack of portions and that can be attached to the belt 164. In the description below, a direction along one side of the stack is taken as an X direction, a direction along another side that is orthogonal to the one side is taken as a Y direction, and a thickness direction of the stack is taken as a Z direction. In addition, a view from the protective portion 151 side in the Z direction is referred to as a plan view.

Figure 4:
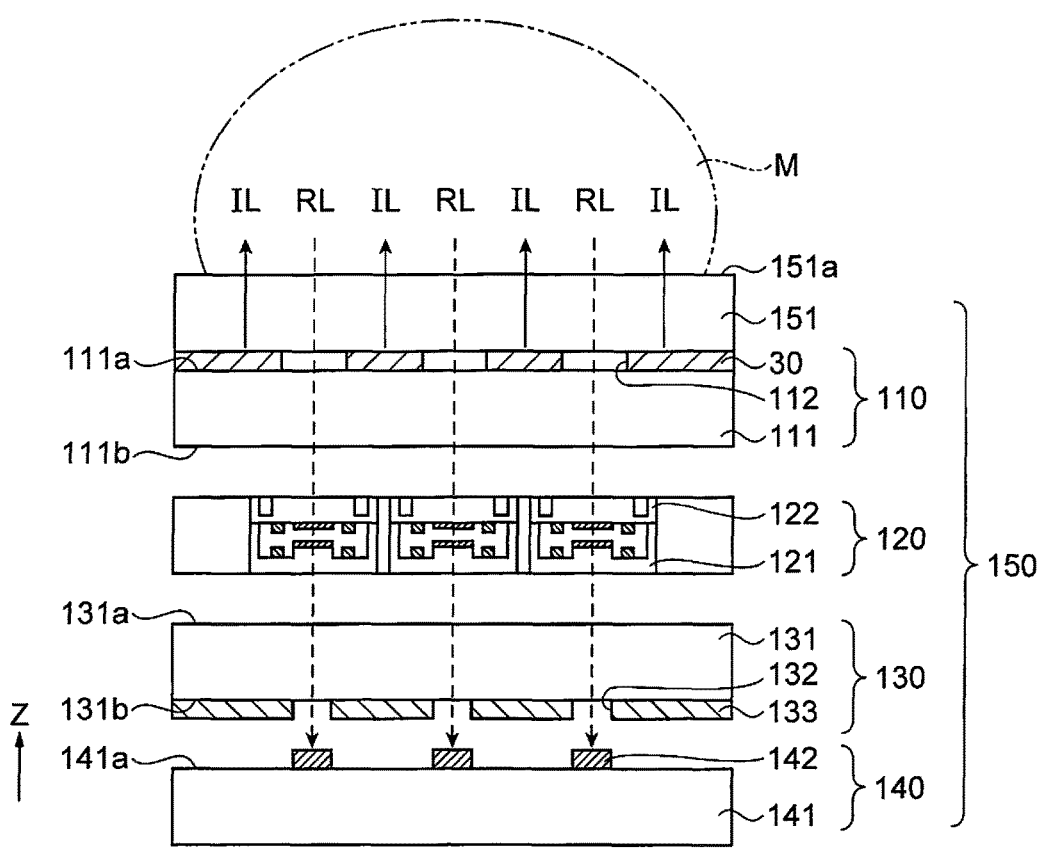
FIG. 4 is a schematic cross-sectional view illustrating a structure of the sensor unit.

As shown in FIG. 4, the light emitting portion 110 includes a light transmissive substrate main body 111, and light source portions 30 and light transmissive portions 112 that are provided on one surface 111a of the substrate main body 111. The protective portion 151 is provided so as to overlap the light source portions 30 and the light transmissive portions 112. The protective portion 151 is a transparent cover glass or a transparent plastic plate, for example. The human body M is positioned so as to come into contact with one surface 151a of the protective portion 151. The light source portions 30 are each configured to emit infrared light IL toward the protective portion 151 side, and reflected light RL, which is a portion of the infrared light IL scattering inside the human body M, passes through the light transmissive portions 112 and is guided to the variable spectral portion 120, which is the underlying layer.

The variable spectral portion 120 is an example of a variable band pass filter, and includes fixed substrates 121 and movable substrates 122. Although the variable spectral portion 120 will be described later in detail, a spectral distribution (spectral characteristics) of the reflected light RL passing through the variable spectral portion 120 can be changed by electrically controlling a gap between the fixed substrate 121 and the movable substrate 122. After passing through the variable spectral portion 120, the reflected light RL is guided to the light blocking portion 130, which is the underlying layer.

The light blocking portion 130 includes a light transmissive substrate main body 131, and a light blocking film 133 provided on a surface 131b of the light blocking portion 131 on a side opposite to a surface 131a thereof on the variable spectral portion 120 side. The light blocking film 133 is provided with openings (pinholes) 132 at positions corresponding to the positions at which the light transmissive portions 112 of the light emitting portion 110 are disposed. The light blocking portion 130 is disposed between the variable spectral portion 120 and the light receiving portion 140 such that only the reflected light RL that passes through the openings 132 is guided to light receiving elements 142 and the rest of the reflected light RL is blocked by the light blocking film 133.

The light receiving portion 140 is an image sensor for infrared light, and includes a substrate main body 141, and a plurality of light receiving elements 142 that are provided on a surface 141a of the substrate main body 141 on the light blocking portion 130 side. For example, a glass epoxy substrate or a ceramic substrate on which the light receiving elements 142 can be mounted can be adopted as the substrate main body 141, and the substrate main body 141 includes an electric circuit (not shown) to which the light receiving elements 142 are connected. The light receiving elements 142 are disposed on the surface 141a of the substrate main body 141 at positions corresponding to the positions at which the openings 132 of the light blocking portion 130 are disposed. An optical sensor such as a CCD or a CMOS can be used as the light receiving element 142. It is known that the sensitivity of the optical sensor varies depending on the wavelength of light. For example, the sensitivity of a CMOS sensor to visible light is higher than that to infrared light IL. If visible light is mixed in infrared light IL that is emitted by the light emitting portion 110 and received via the human body M, the visible light causes noise output by the CMOS sensor. The variable spectral portion 120 according to this embodiment is configured such that a transmittance of visible light is lower than a transmittance of near-infrared light IL having a wavelength of 700 to 2000 nm.

It should be noted that filters for blocking light in a wavelength range of visible light (400 to 700 nm) may be disposed corresponding to the light transmissive portions 112 of the light emitting portion 110 and the openings 132 of the light blocking portion 130.

The protective portion 151, the light emitting portion 110, the variable spectral portion 120, the light blocking portion 130, and the light receiving portion 140 are disposed so as to be opposed to one another with gaps therebetween, and are attached to one another using an adhesive (not shown in FIG. 4) or the like.

It should be noted that the configuration of the sensor unit 150 is not limited to this. For example, the light emitting portion 110 may be configured to include the protective portion 151 or may have a configuration in which the light source portions 30 are sealed by the protective portion 151. Moreover, since there is a risk that light passing through the light transmissive portions 112 will be reflected at the interface between members that have different refractive indices and attenuated, the light emitting portion 110 and the variable spectral portion 120 may be attached to each other such that a surface 111b of the substrate main body 111 of the light emitting portion 110 comes into contact with the variable spectral portion 120, for example. Also, the variable spectral portion 120 and the light blocking portion 130 may be attached to each other such that the variable spectral portion 120 comes into contact with the surface 131a of the light blocking portion 130. Thereby, positional relationships therebetween in the thickness direction (Z direction) can be better secured.

Figure 5:
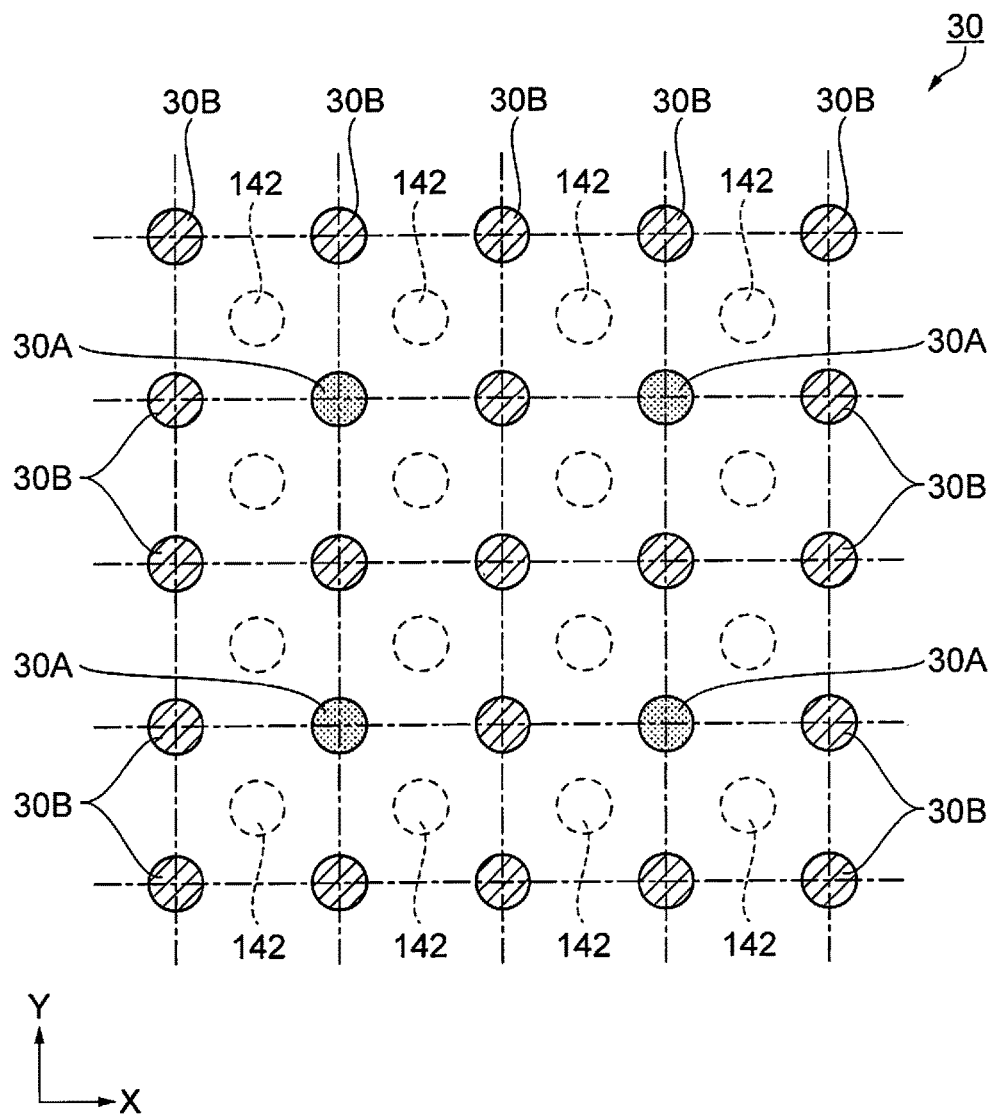
FIG. 5 is a schematic plan view illustrating an arrangement of first light emitting elements and second light emitting elements.
Figure 6:
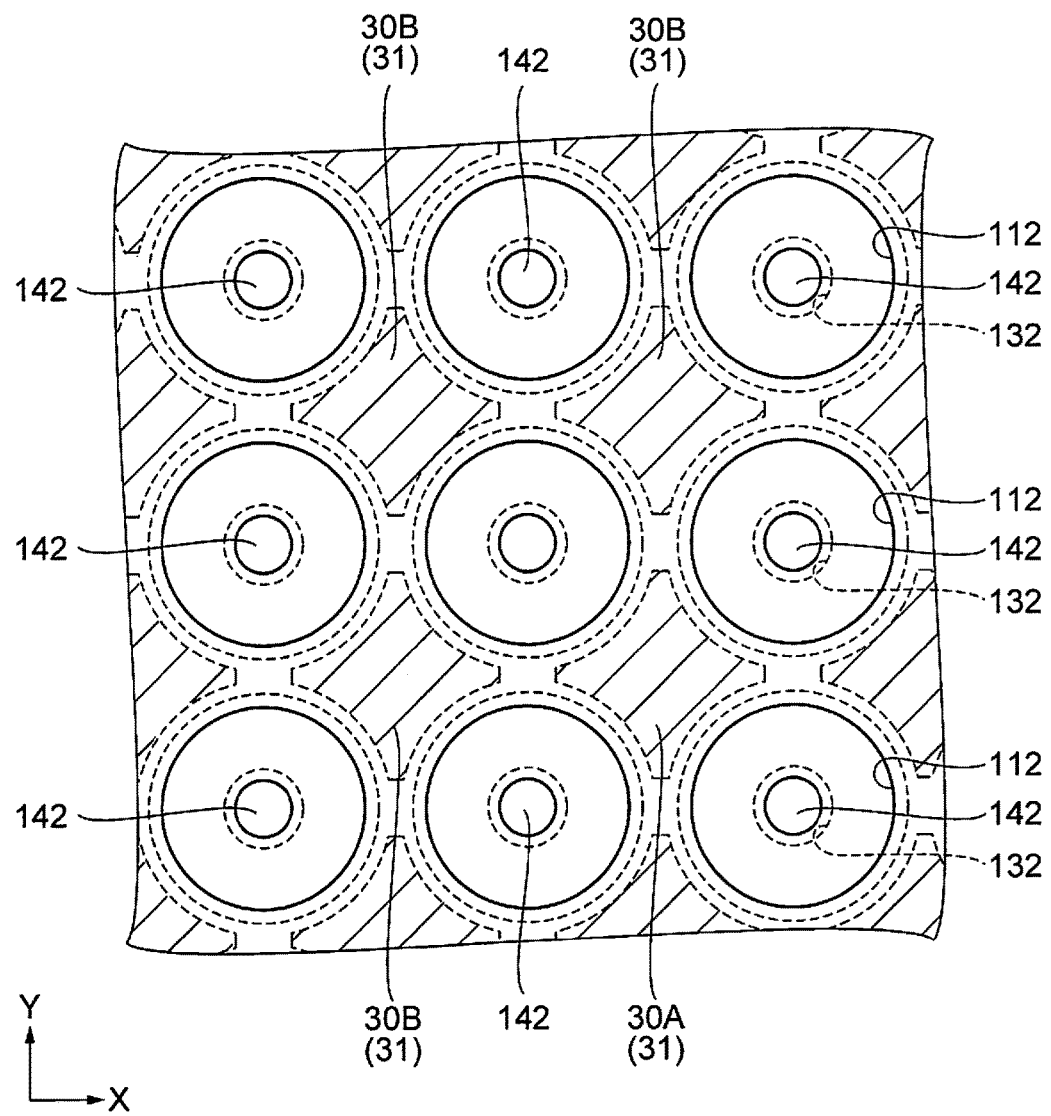
FIG. 6 is a schematic plan view illustrating a specific arrangement of light receiving elements, the first light emitting elements and the second light emitting elements.
Figure 7:
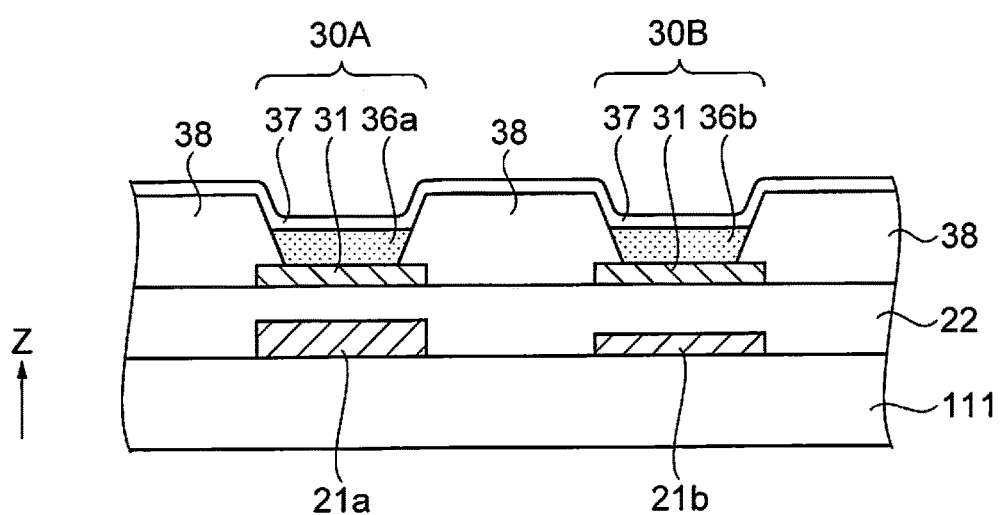
FIG. 7 is a schematic cross-sectional view illustrating structures of the first light emitting element and the second light emitting element.
Figure 8:
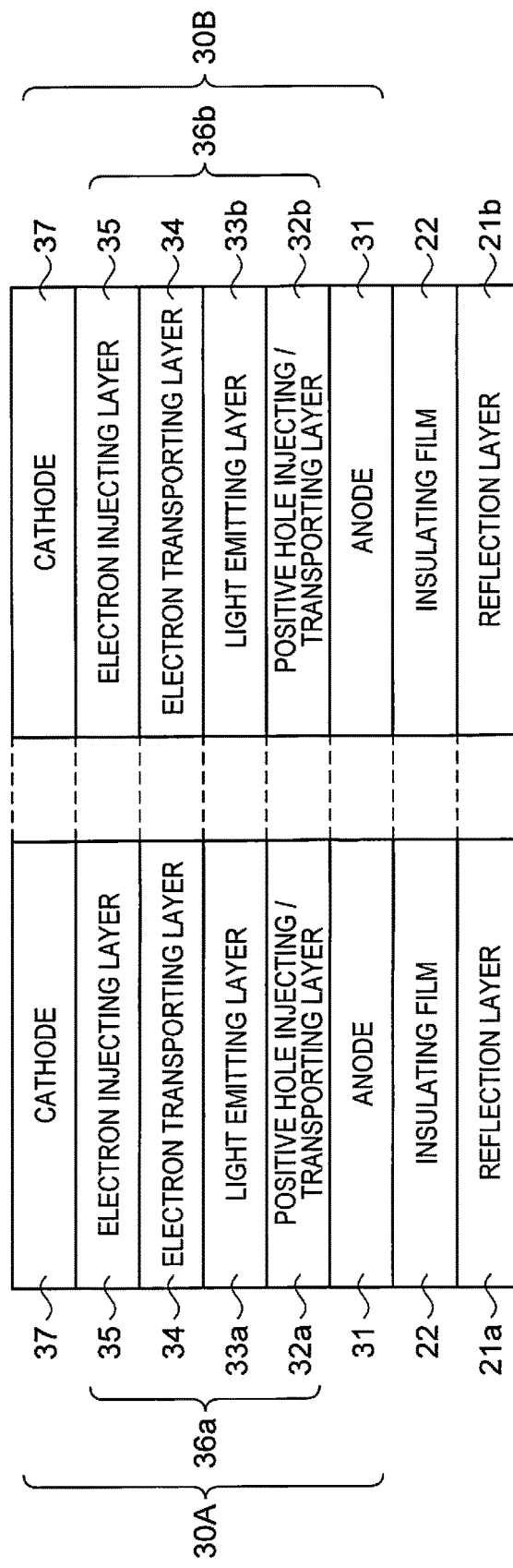
FIG. 8 is a schematic cross-sectional view illustrating configurations of the first light emitting element and the second light emitting element.

Next, the configuration of the light source portion 30 will be described with reference to FIGS. 5 to 8. FIG. 5 is a schematic plan view illustrating an arrangement of the first light emitting elements and the second light emitting elements. FIG. 6 is a schematic plan view illustrating a specific arrangement of the light receiving elements, the first light emitting elements and the second light emitting elements. FIG. 7 is a schematic cross-sectional view illustrating structures of the first light emitting element and the second light emitting element. FIG. 8 is a schematic cross-sectional view illustrating configurations of the first light emitting element and the second light emitting element.

As shown in FIG. 5, the light source portion 30 includes a plurality of first light emitting elements 30A serving as first infrared light sources and a plurality of second light emitting elements 30B serving as second infrared light sources. The first light emitting elements 30A and the second light emitting elements 30B are arranged in a matrix in the X direction and the Y direction. Specifically, unit pixels including one light receiving element 142 are arranged in a matrix in the X direction and the Y direction. The light receiving element 142 is disposed at the center of the unit pixel, which is square in a plan view, the first light emitting element 30A is disposed at one corner of the square unit pixel, and the second light emitting elements 30B are disposed at the remaining three corners thereof. The first light emitting elements 30A are used as lighting (light source) for acquiring positional information of blood vessels in the human body M, and are arranged at equal intervals (in this case, intervals correspond to two unit pixels arranged) in the X direction and the Y direction. On the other hand, the second light emitting elements 30B are used as lighting (light source) for acquiring information of the amount of a specific component contained in blood and the like, and the number of second light emitting elements 30B arranged is larger than that of the first light emitting elements 30A in order to ensure the amount of light. In the unit pixel, the ratio of the number of first light emitting elements 30A to the number of second light emitting elements 30B is one to three.

In this embodiment, the first light emitting elements 30A and the second light emitting elements 30B are configured by organic electroluminescent elements (referred to as "organic EL elements" hereinafter).

An organic EL element is thin, and includes an anode, a cathode, and a functional layer that is sandwiched between these electrodes and has a light emitting function. The shape and arrangement of the organic EL element can be set relatively freely.

It is known that an organic EL element can emit not only visible light such as monochromatic light of red, green and blue, and white light in which these colors are used in combination but also invisible infrared light IL by selecting materials constituting a light emitting layer included in the functional layer.

As shown in FIG. 6, in this embodiment, the light transmissive portions 112 for guiding the reflected light RL from the human body M to the light receiving elements 142 are arranged in a matrix in the X direction and the Y direction. The light transmissive portions 112 each have a circular shape around the light receiving element 142 as a center in a plan view in order to uniformly guide the reflected light RL to the light receiving elements 142. Light receiving surfaces of the light receiving elements 142 each also have a circular shape, and the openings 132 of the light blocking portion 130 each have a circular shape centered on the light receiving element 142.

Accordingly, the first light emitting elements 30A and the second light emitting elements 30B disposed between the light transmissive portions 112 each have a substantially diamond shape surrounded by circular arcs in a plan view. In this embodiment, the first light emitting elements 30A and the second light emitting elements 30B each have a shape defined by the shape of an anode 31 that is in contact with the functional layer in a plan view.

As shown in FIG. 7, the first light emitting elements 30A and the second light emitting elements 30B are formed on the substrate main body 111. Specifically, reflection layers 21a and 21b are formed in an insular shape on the substrate main body 111, using an alloy having light reflecting properties, such as an alloy of aluminum (Al) and neodymium (Nd). The reflection layer 21a is thicker than the reflection layer 21b.

Next, an interlayer insulating film 22 for covering the reflection layers 21a and 21b is formed using light transmissive silicon oxide, for example. Since the interlayer insulating film 22 covers the reflection layers 21a and 21b, which are different in thickness, the surface thereof become uneven. Therefore, planarizing processing such as CMP processing is performed in order to reduce the unevenness. The anodes 31 are formed in an insular shape on the planarized interlayer insulating film 22, using a transparent conductive film such as an ITO film. The thickness of the interlayer insulating film 22 existing between the reflection layer 21a and the anode 31 is thinner (smaller) than the thickness of the interlayer insulating film 22 existing between the reflection layer 21b and the anode 31.

Next, a photosensitive resin layer is formed so as to cover the anodes 31, and partition walls 38 that overlap the outer edge portions of the anodes 31 and from which the anodes 31 are exposed are formed by exposing and developing the photosensitive resin layer by photolithography. The partition walls 38 are formed so as to partition the anodes 31 adjacent to each other.

Next, a functional layer 36a is formed in a region surrounded by the partition walls 38 on the anode 31 opposed to the reflection layer 21a. Also, a functional layer 36b is formed in a region surrounded by the partition walls 38 on the anode 31 opposed to the reflection layer 21b. Although the layer configurations of the functional layers 36a and 36b will be described later, the functional layers 36a and 36b may have the same layer configuration or different layer configurations.

Next, a cathode 37 is formed so as to cover the functional layers 36a and 36b, and the partition walls 38. The cathode 37 is formed using an alloy of Ag and Mg, for example, so as to have both light reflecting properties and light transmitting properties by controlling the film thickness. It should be noted that the cathode 37 is not limited to the layer made of an alloy of Ag and Mg, and may have a multilayer structure in which a layer made of Mg is stacked on a layer made of an alloy of Ag and Mg, for example.

Thereby, the first light emitting element 30A including the anode 31, the functional layer 36a and the cathode 37 is formed above the reflection layer 21a on the substrate main body 111. In addition, the second light emitting element 30B including the anode 31, the functional layer 36b and the cathode 37 is formed above the reflection layer 21b on the substrate main body 111.

A portion of light emitted by the functional layer 36a passes through the anode 31, is reflected by the reflection layer 21a, passes through the cathode 37, and then is emitted outward. Similarly, a portion of light emitted by the functional layer 36b passes through the anode 31, is reflected by the reflection layer 21b, passes through the cathode 37, and then is emitted outward. That is, the first light emitting element 30A and the second light emitting element 30B are top emission type light emitting elements. Since the cathode 37 has light reflecting properties as described above, a portion of light emitted by the functional layer 36a of the first light emitting element 30A is repeatedly reflected between the cathode 37 and the reflection layer 21a, the intensity of light having a specific wavelength based on the optical distance between the cathode 37 and the reflection layer 21a is increased, and the light is emitted outward. That is, an optical resonance structure in which the intensity of light having a specific wavelength is increased is introduced into the first light emitting element 30A.

On the other hand, although a portion of light emitted by the functional layer 36b of the second light emitting element 30B is also reflected between the cathode 37 and the reflection layer 21b, the second light emitting element 30B has a structure in which the intensity of light having a specific wavelength is unlikely to be increased because the distance between the anode 31 of the second light emitting element 30B and the reflection layer 21b is larger than the distance between the anode 31 of the first light emitting element 30A and the reflection layer 21a (that is, the anode 31 of the second light emitting element 30B and the reflection layer 21b are farther apart from each other).

It should be noted that although not shown in FIG. 7, driving circuits that apply current between the anode 31 and the cathode 37 and enable the functional layer 36a and the functional layer 36b to independently emit light are provided on the substrate main body 111 for the respective first light emitting elements 30A and second light emitting elements 30B.

Next, the layer configurations of the functional layers 36a and 36b will be described with reference to FIG. 8. As shown in FIG. 8, the functional layer 36a sandwiched between the anode 31 and the cathode 37 in the first light emitting element 30A includes a positive hole injecting/transporting layer 32a, a light emitting layer 33a, an electron transporting layer 34, and an electron injecting layer 35. The functional layer 36b sandwiched between the anode 31 and the cathode 37 in the second light emitting element 30B includes a positive hole injecting/transporting layer 32b, a light emitting layer 33b, an electron transporting layer 34, and an electron injecting layer 35.

Positive Hole Injecting/Transporting Layers

The positive hole injecting/transporting layers 32a and 32b have a function for transporting, to the light emitting layers 33a and 33b, positive holes transferred from the anode 31. Accordingly, it is preferable that a positive hole injecting/transporting material contained in the positive hole injecting/transporting layers 32a and 32b has both positive hole injecting properties and positive hole transporting properties, and it is preferable to use an aromatic amine compound, represented by the following chemical formula (1), in which a portion A of the skeleton is selected from a phenylenediamine series, a benzidine series and a terphenylenediamine series.

Chemical Formula 1

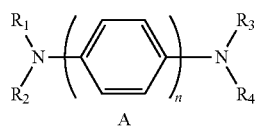  (1)

R1 to R4 independently represent a substituted or nonsubstituted aromatic functional group, and particularly preferably a substituted or nonsubstituted aryl functional group, and a phenyl group, biphenyl group, terphenyl group and a triarylamino group are preferable. n represents a number from one to three.

Examples of a phenyldiamine-based compound in which n of A is one include compounds represented by the following chemical formulae HTL1 to HTL7.

Chemical Formula 2

HTL1

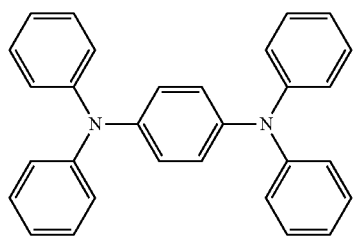

HTL2

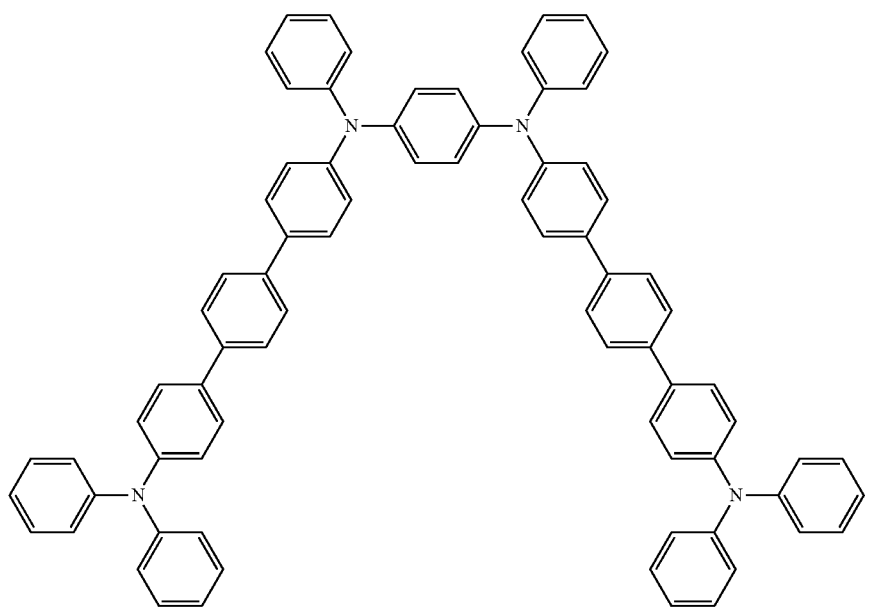

HTL3

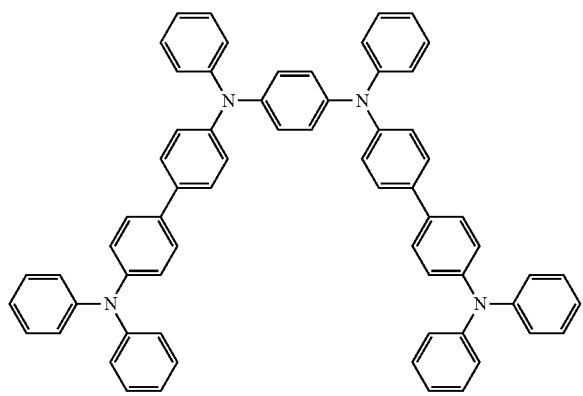

HTL4

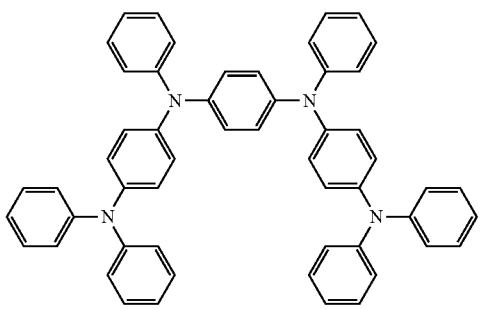

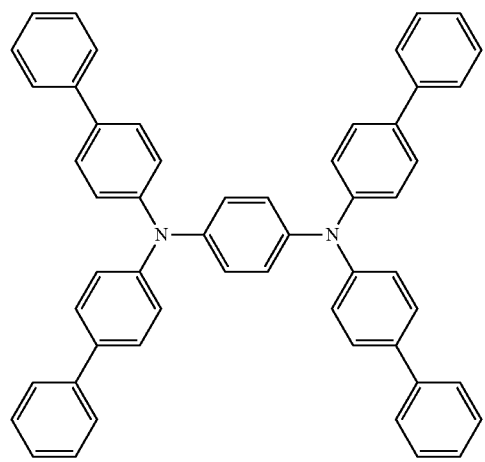
HTL5
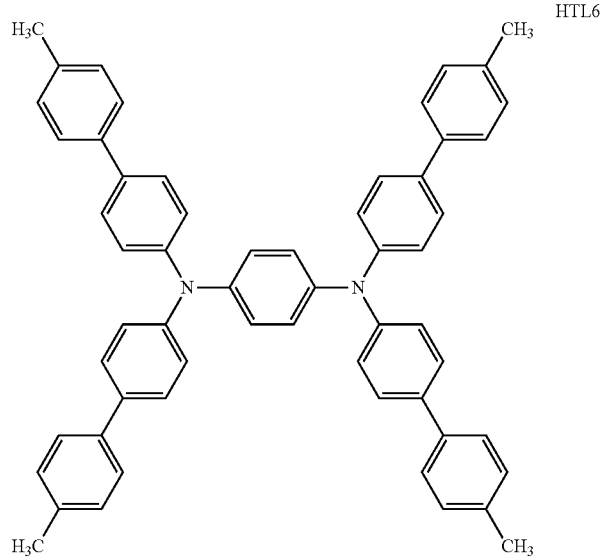
HTL6
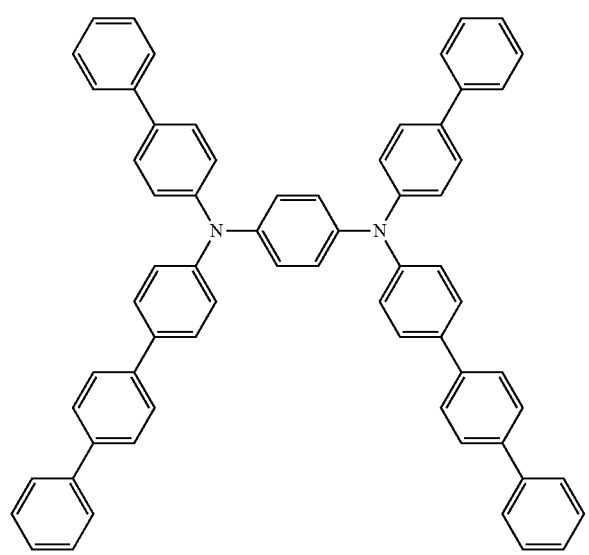
HTL7
Examples of a benzidine-based compound in which n of A is two include compounds represented by the following chemical formulae HTL8 to HTL16.
Chemical Formula 3
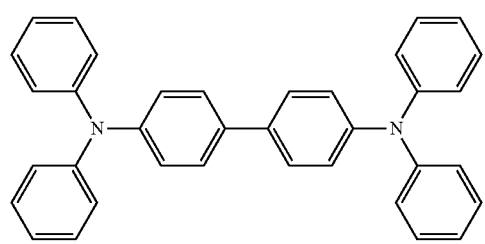
HTL8

-continued
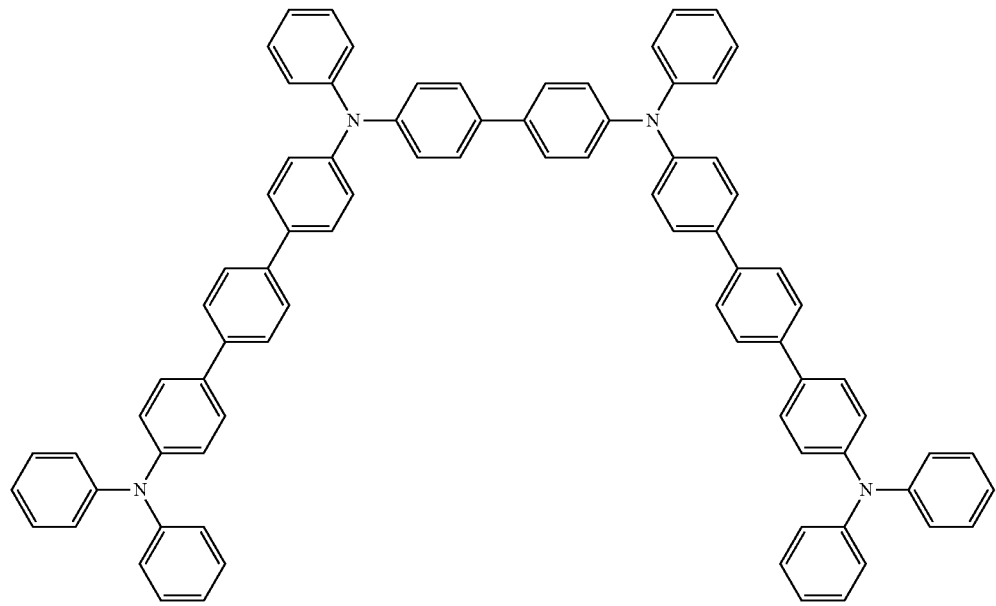
HTL9
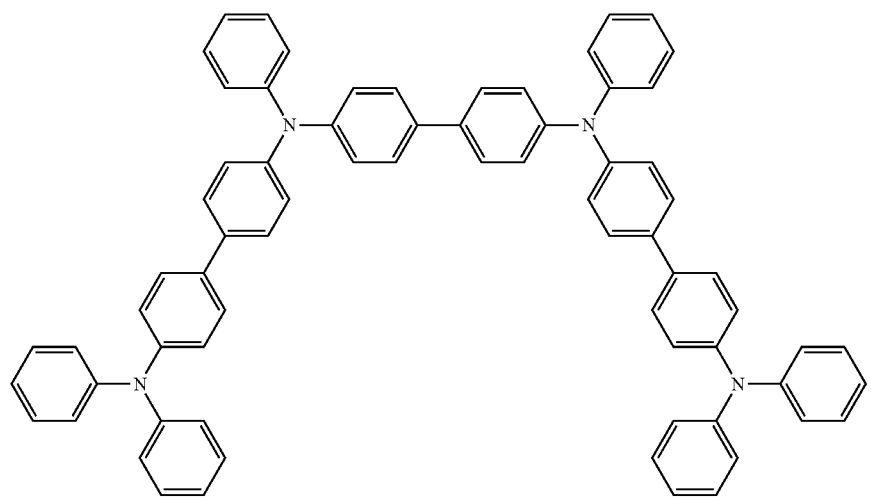
HTL10
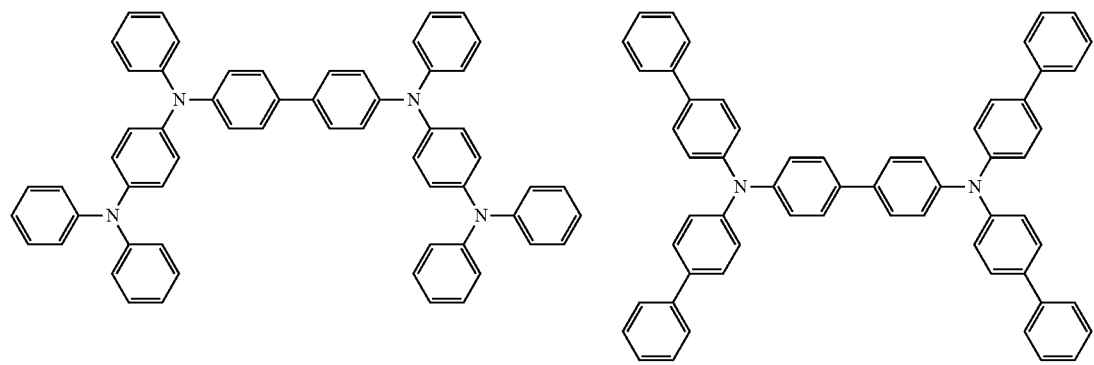
HTL11    HTL12

HTL13
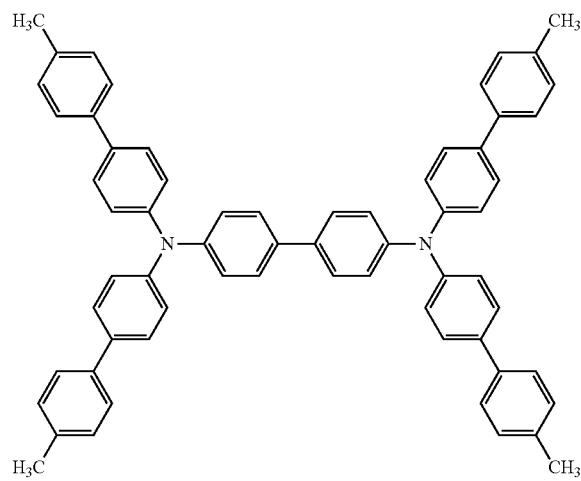
HTL14
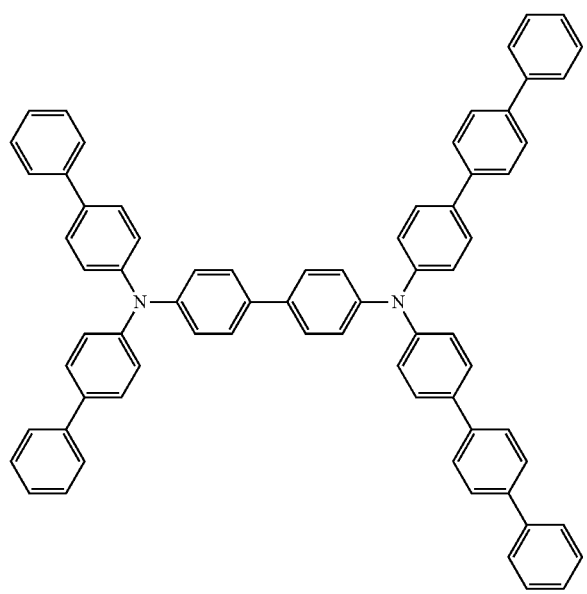
HTL15
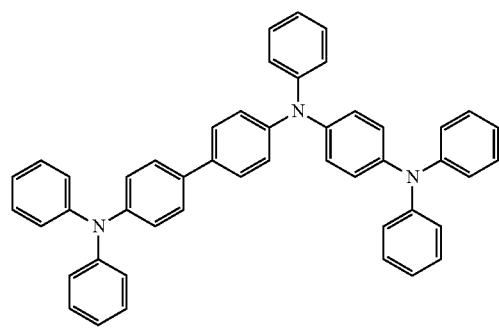
HTL16
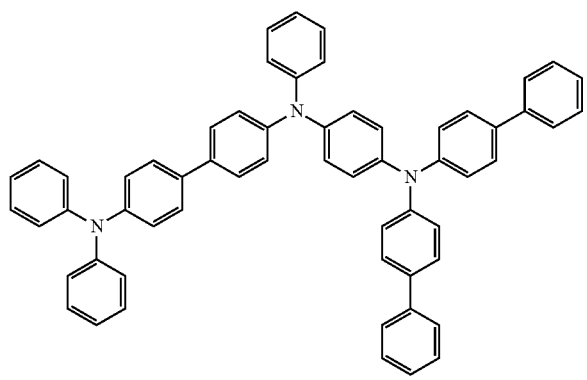
Examples of a terphenylenediamine-based compound in which n of A is three include compounds represented by the following chemical formulae HTL17 to HTL25.
Chemical Formula 4
HTL17
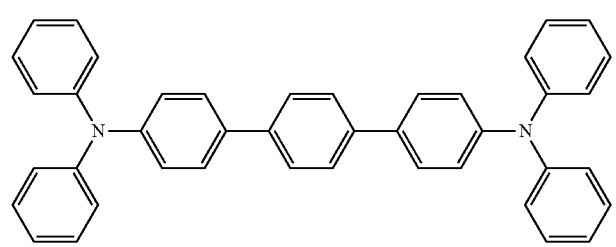

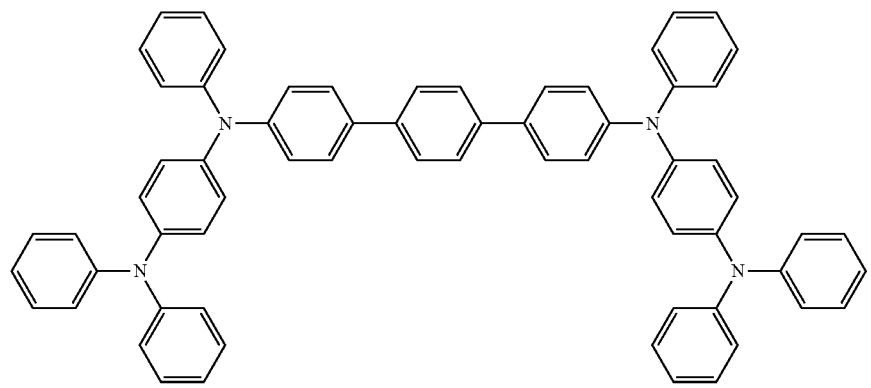
HTL18
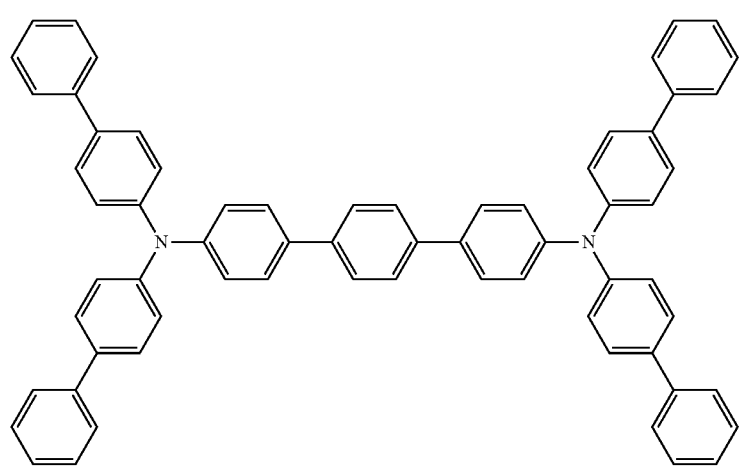
HTL19
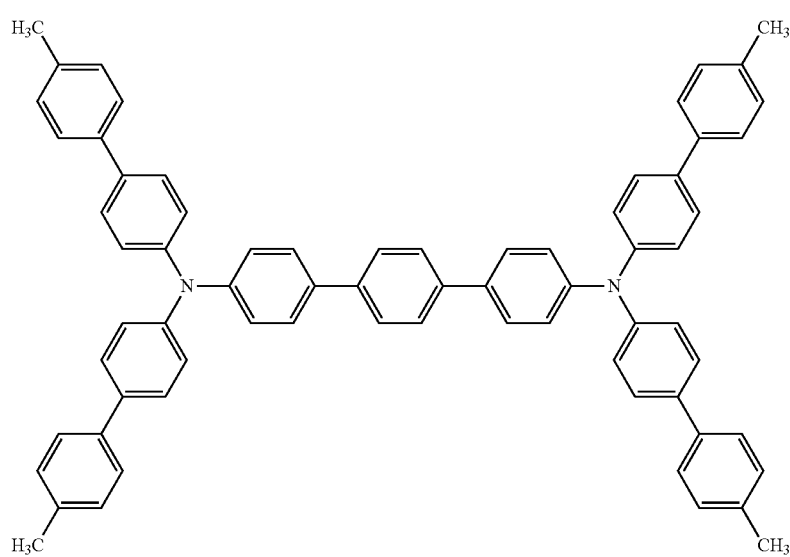
HTL20

-continued
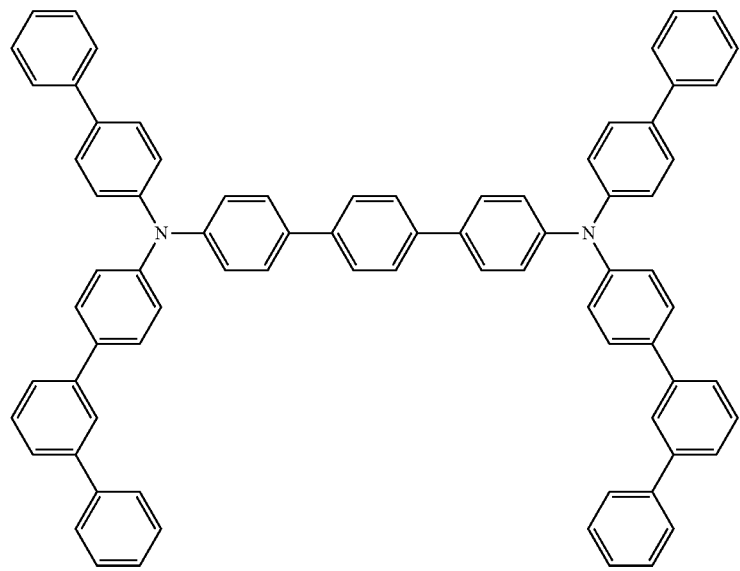
HTL21
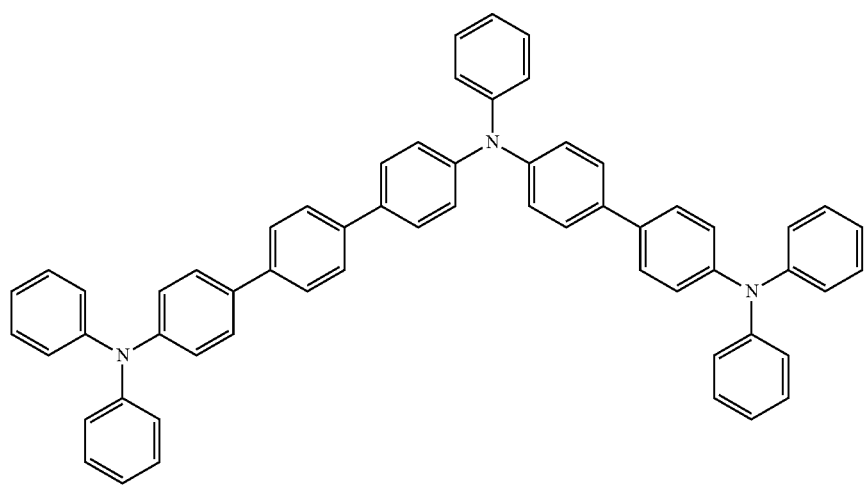
HTL22
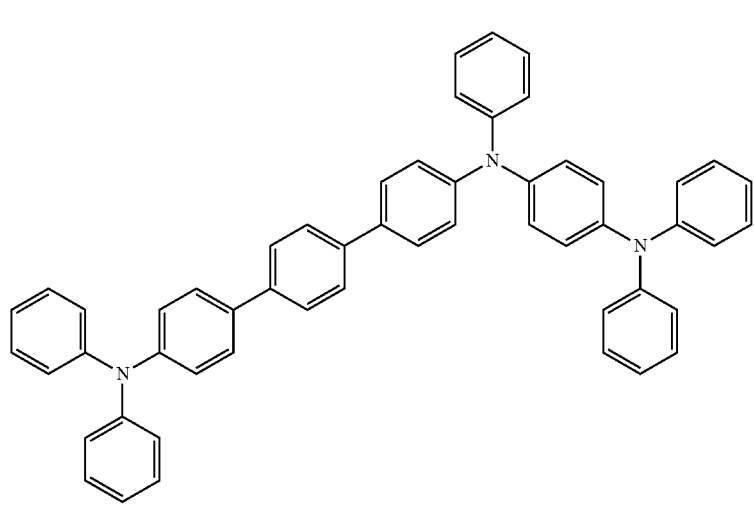
HTL23

-continued

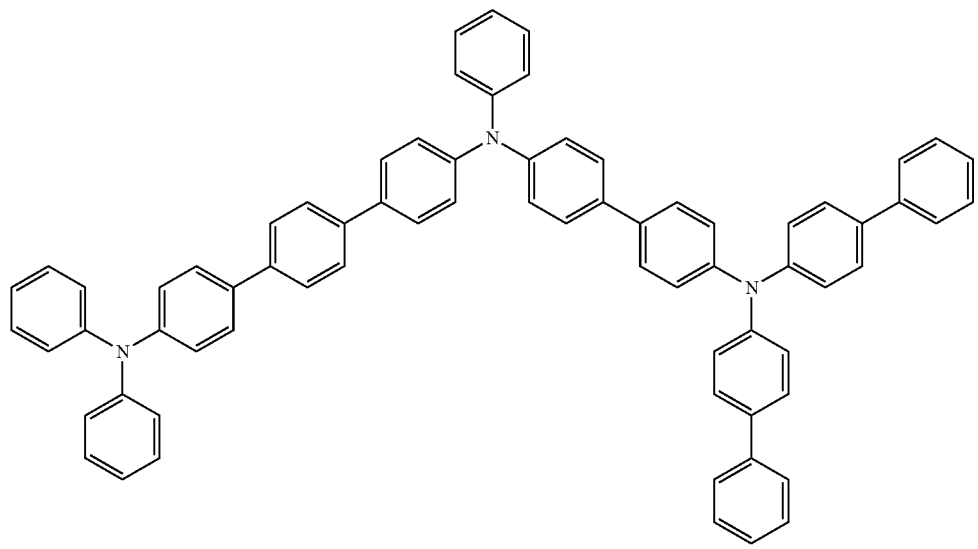

HTL24

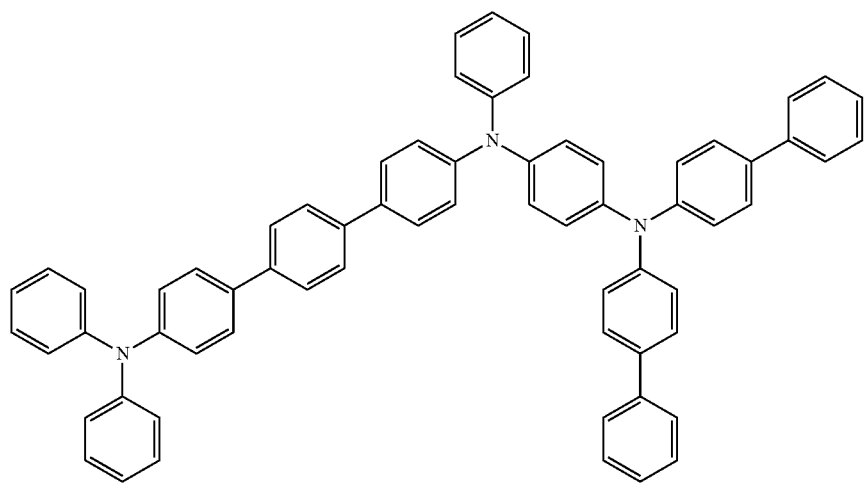

HTL25

The average thickness of such positive hole injecting/transporting layers 32a and 32b is preferably about 5 to 200 nm, and more preferably about 10 to 100 nm, but is not particularly limited thereto.

It should be noted that the first light emitting element 30A is not limited to the case where only the positive hole injecting/transporting layer 32a is provided between the anode 31 and the light emitting layer 33a. A plurality of layers including a positive hole injecting layer to which positive holes are easily injected from the anode 31 and a positive hole transporting layer from which positive holes are easily transported to the light emitting layer 33a may be provided therebetween, for example. In addition, a layer having a function for blocking electrons that leak from the light emitting layer 33a to the anode 31 side may be included. The same applies to the positive hole injecting/transporting layer 32b between the anode 31 and the light emitting layer 33b in the second light emitting element 30B.

Light Emitting Layer

The light emitting layers 33a and 33b include a compound (also referred to merely as a "thiadiazole-based compound" or a "selenadiazole-based compound" hereinafter) represented by the following chemical formula (5) as the basic skeleton.

Chemical Formula 5

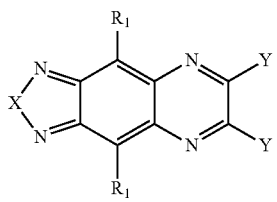

(5)

In the chemical formula (5), X represents S or Se, and Y represents a functional group and may form a ring.

Specifically, it is preferable to use thiadiazole-based compounds represented by the following chemical formulae EML1 to EML8.

[Chemical Formula 6]
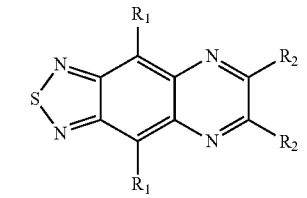
EML1
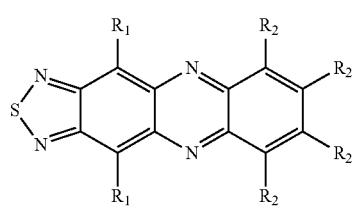
EML2
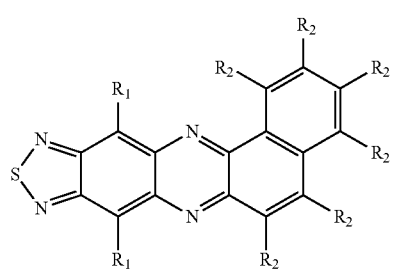
EML3
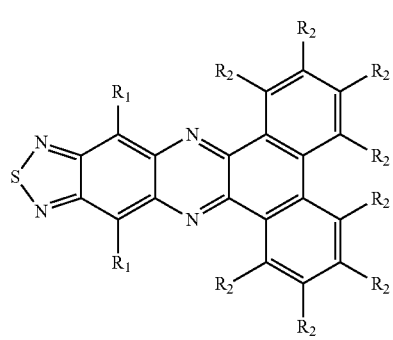
EML4
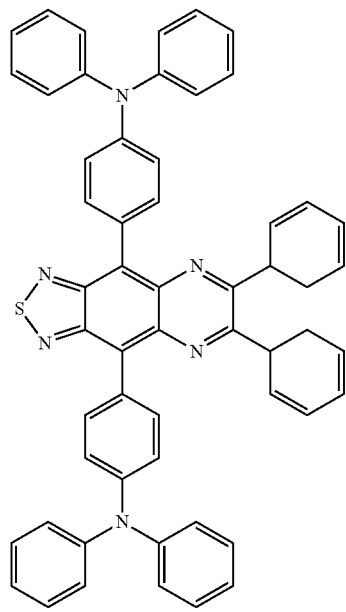
EML5
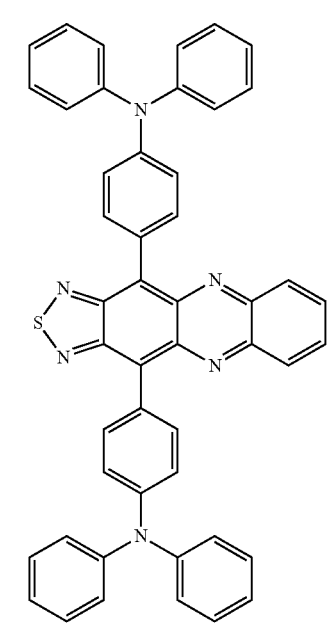
EML6

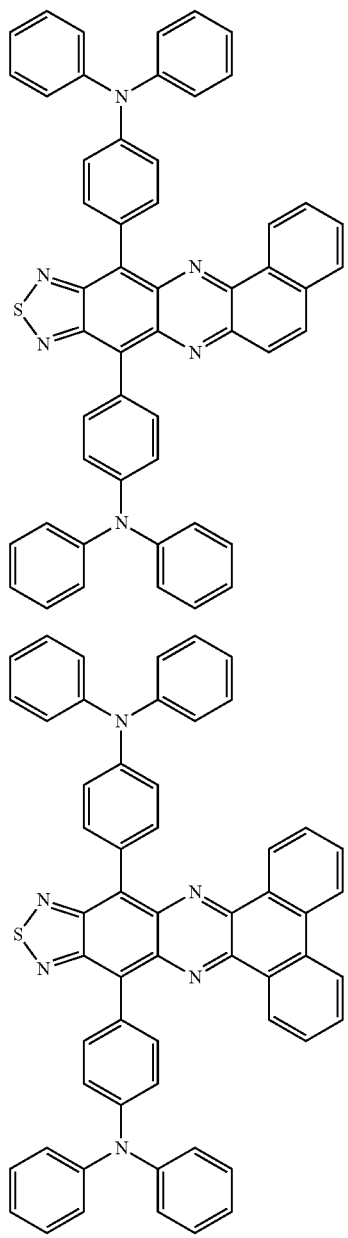

R1 is preferably an aromatic compound (that may or may not have a substituent group). An aryl group, an aryl group having a substituent group, an arylamino group and a thiophenyl group are particularly preferable. A phenyl group and a naphthyl group are preferable as the aryl group. A triphenylamino group is preferable as the aryl group having a substituent group.

R2 is preferably a hydrogen atom, an alkyl group, an alkoxy group, an ester group or an aromatic compound (that may or may not have a substituent group). An aryl group, an aryl group having a substituent group, an arylamino group and a thiophenyl group are particularly preferable. A phenyl group and a naphthyl group are preferable as the aryl group.

The light emitting layers 33a and 33b including such compounds can emit light in a wavelength region (infrared region) of 700 to 2000 nm.

It should be noted that the light emitting layers 33a and 33b may include light emitting materials (various fluorescent materials, various phosphorescent materials) other than the light emitting materials described above. Moreover, the light emitting layer 33b may include a light emitting material that is different from that included in the light emitting layer 33a. In this case, in response to the light emitting layer 33b, the positive hole injecting/transporting layer 32b may include a positive hole injecting/transporting material that is different from that included in the positive hole injecting/transporting layer 32a.

Furthermore, in addition to the light emitting materials, a host material to which this light emitting material is added (or that carries this light emitting material) as a guest material (dopant) is used as a component material of the light emitting layers 33a and 33b. This host material has a function for recombining positive holes and electrons to produce excitons, and for transferring the energy of the excitons to the light emitting material (Förster transfer or Dexter transfer) to excite the light emitting material. This makes it possible to enhance the light emission efficiency. Such a host material is used by doping the host material with the light emitting material serving as a guest material as a dopant, for example.

It is particularly preferable to use a quinolinolato metal complex or an acene-based organic compound as such a host material. As an acene-based material, an anthracene-based material and a tetracene-based material are preferable, and the tetracene-based material is more preferable. When the host material of the light emitting layer includes the acene-based material, electrons can be efficiently transferred from an electron transporting material in the electron transporting layer to the acene-based material in the light emitting layer (EML).

Moreover, the acene-based material has superior durability against electrons and positive holes. The acene-based material also has superior thermal stability. This makes it possible to realize a long life for the first light emitting element 30A and the second light emitting element 30B. Since the acene-based material has superior thermal stability, it is possible to prevent decomposition of the host material due to the heat produced during the formation of the film when the light emitting layer is formed by a vapor-phase film deposition method. Therefore, the light emitting layer having superior film quality can be formed. As a result, in this regard as well, it is possible to enhance the light emission efficiency of the first light emitting element 30A and the second light emitting element 30B and to realize a long life.

Furthermore, since the acene-based material itself is unlikely to emit light, it is possible to prevent the host material from adversely affecting the light emission spectra of the first light emitting element 30A and the second light emitting element 30B.

There is no particular limitation on the tetracene-based material as long as the tetracene-based material has at least one tetracene skeleton in one molecule and can exhibit a function as the host material. For example, it is preferable to use a compound having the basic skeleton represented by the following chemical formula IRH-1, it is more preferable to use a compound represented by the following chemical formula IRH-2, and it is even more preferable to use a compound represented by the following chemical formula IRH-3. This makes it possible to suppress an increase in voltage during continuous driving, to further enhance the light emission efficiency of the first light emitting element 30A and the second light emitting element 30B, and to realize a long life.

Chemical Formula 7

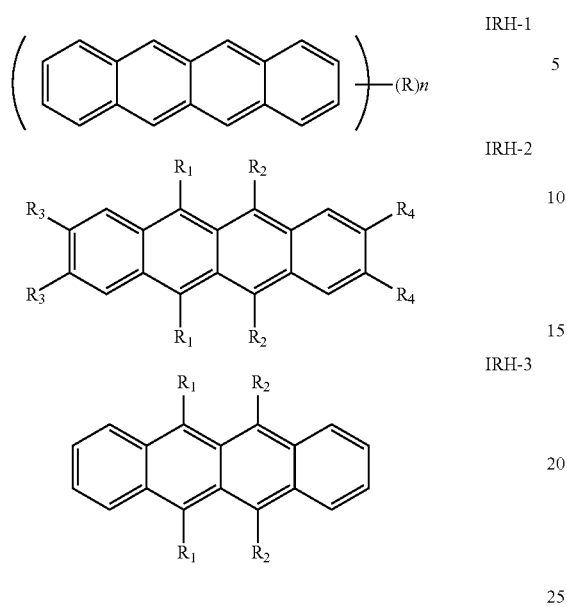

IRH-1

IRH-2

IRH-3

In the chemical formula IRH-1, n represents a natural number from 1 to 12, R represents a substituent or a functional group, and each R independently represents a hydrogen atom, an alkyl group, an aryl group that may have a substituent, or an arylamino group. In the chemical formulae IRH-2 and IRH-3, R1 to R4 independently represent a hydrogen atom, an alkyl group, an aryl group that may have a substituent, or an arylamino group. Moreover, R1 to R4 may be the same as or different from each other.

Moreover, it is preferable that the tetracene-based material used as the host material is constituted by carbon atoms and hydrogen atoms. This makes it possible to prevent the host material and the light emitting material from unintentionally interacting with each other. Therefore, the light emission efficiency of the first light emitting element 30A and the second light emitting element 30B can be improved. Also, the durability thereof against electrons and positive holes can be improved. This makes it possible to suppress an increase in voltage during continuous driving, and to realize a long life for the first light emitting element 30A and the second light emitting element 30B.

Specifically, it is preferable to use compounds represented by the following chemical formulae H-1 to H-27 as the tetracene-based material, for example.

Chemical Formula 8

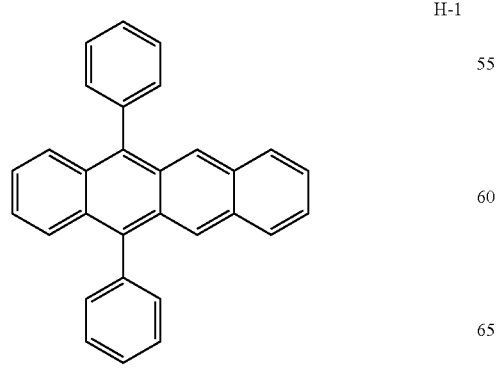

H-1

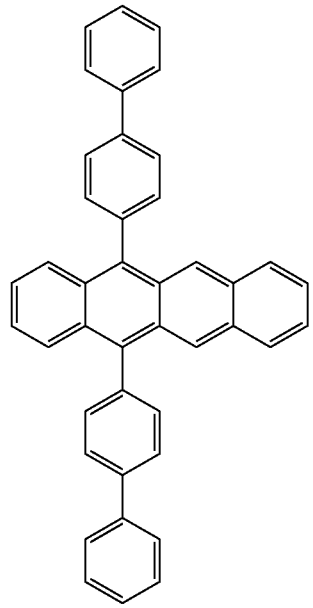

H-2

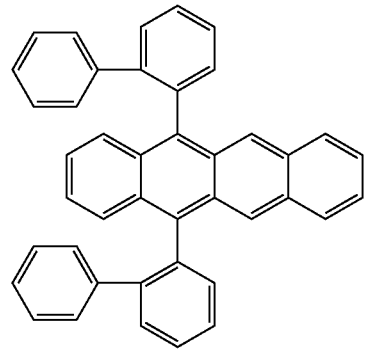

H-3

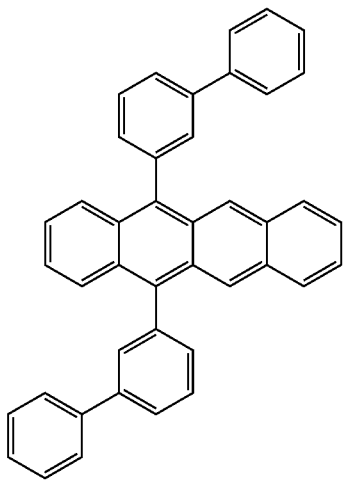

H-4

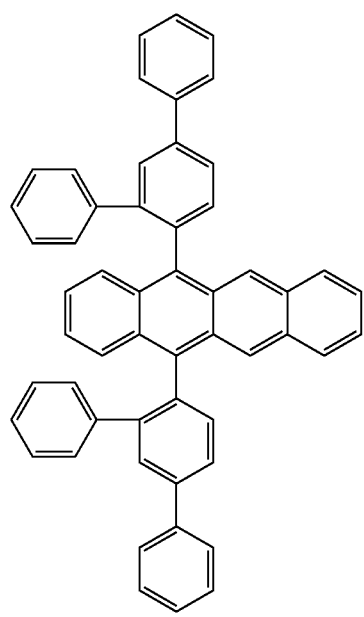
H-5
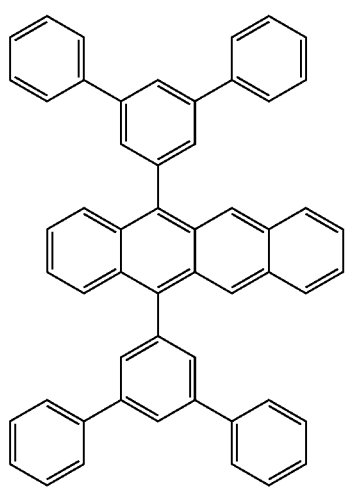
H-8
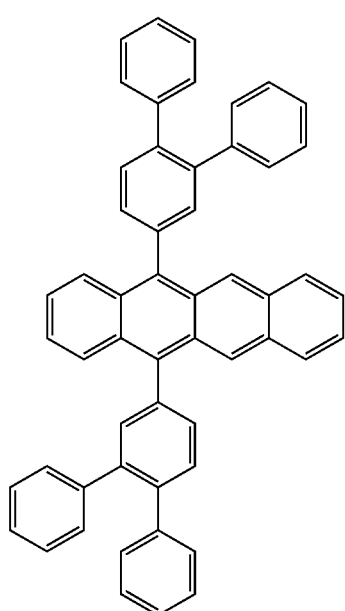
H-9
H-6
H-7

-continued
H-10
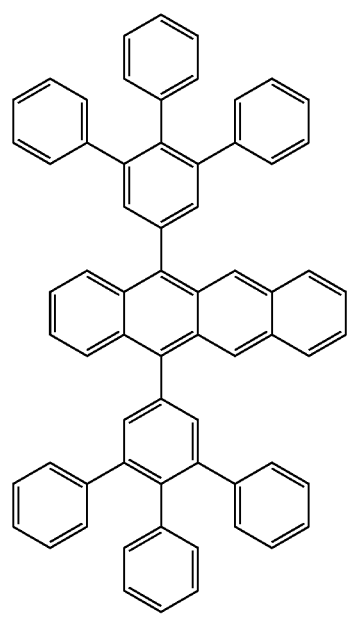
H-11
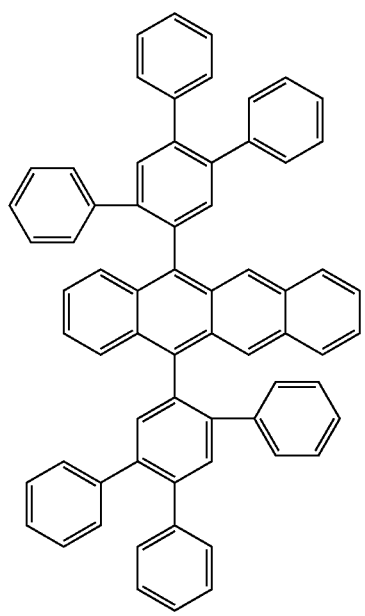
Chemical Formula 9
H-12
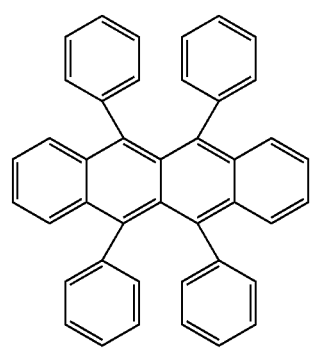
-continued
H-13
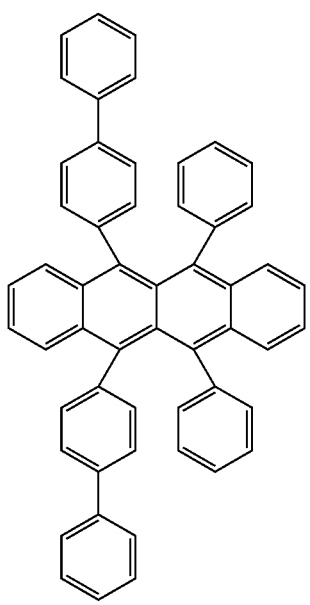
H-14
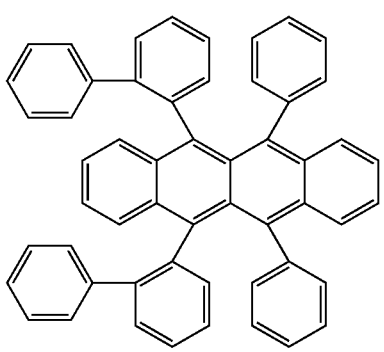
H-15
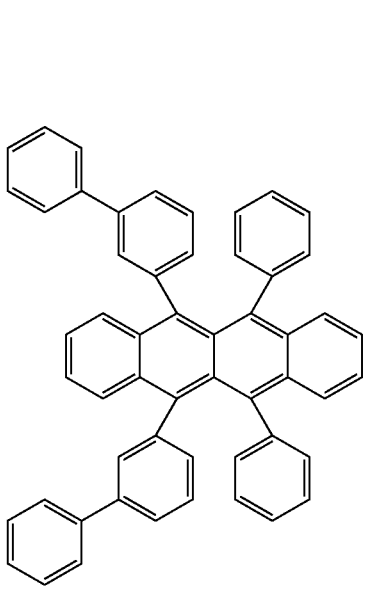

H-16
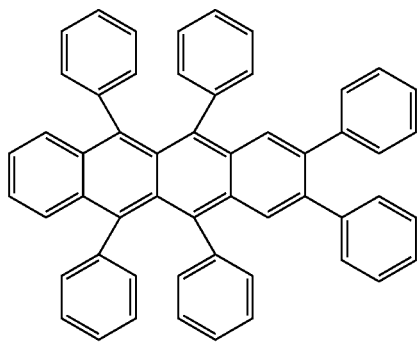
H-19
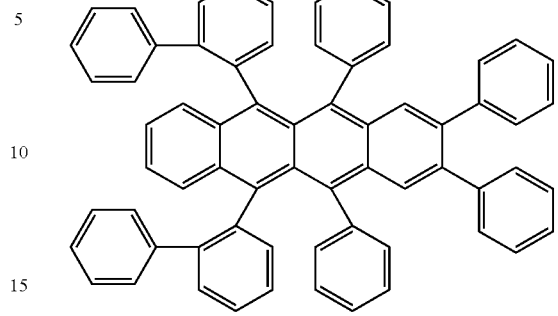
H-17
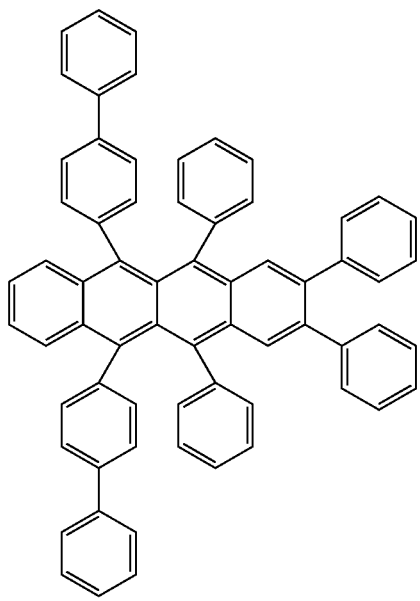
H-20
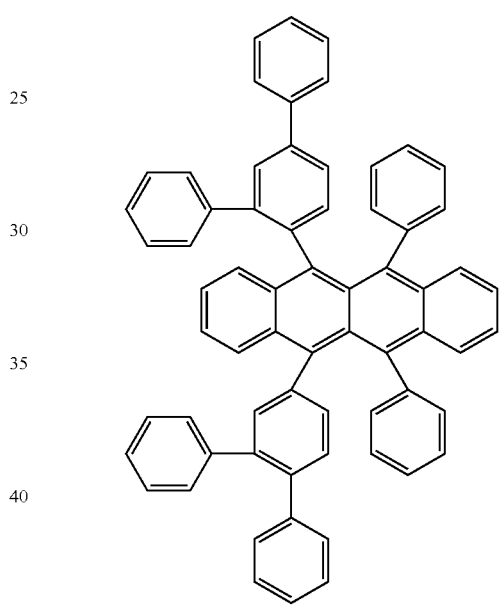
H-18
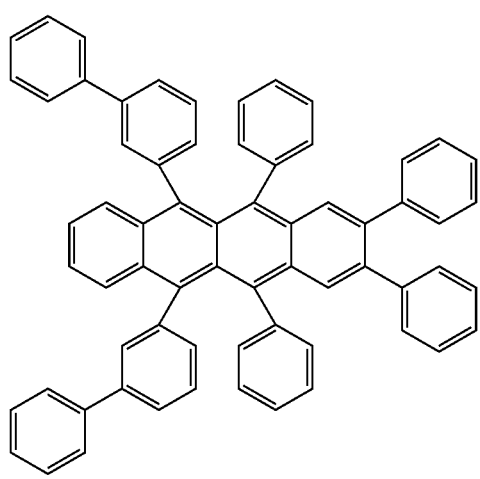
H-21
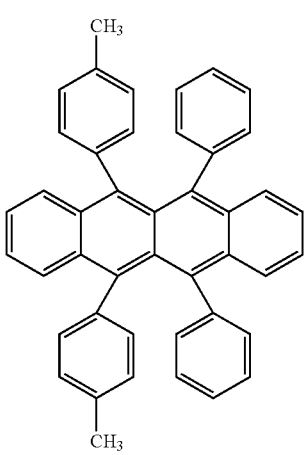

H-22

H-23

H-24

H-25

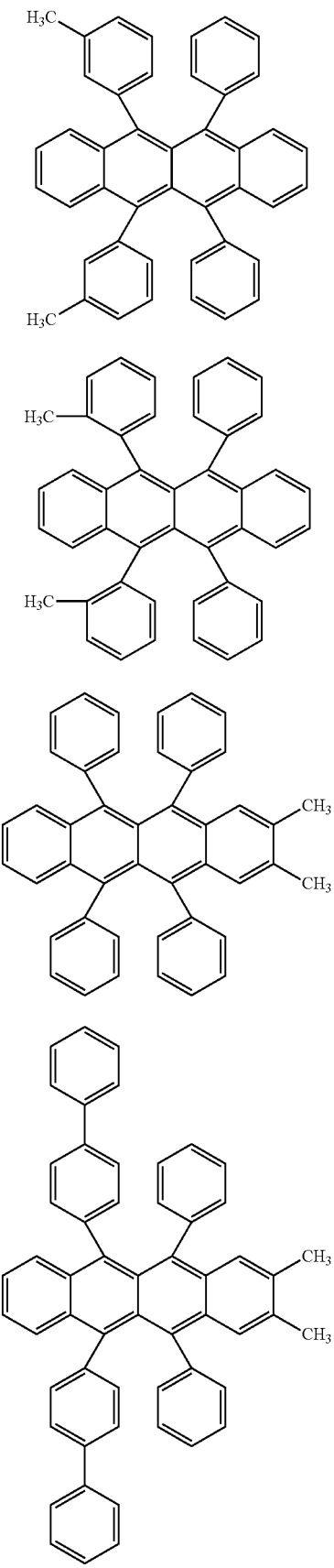

H-26

H-27

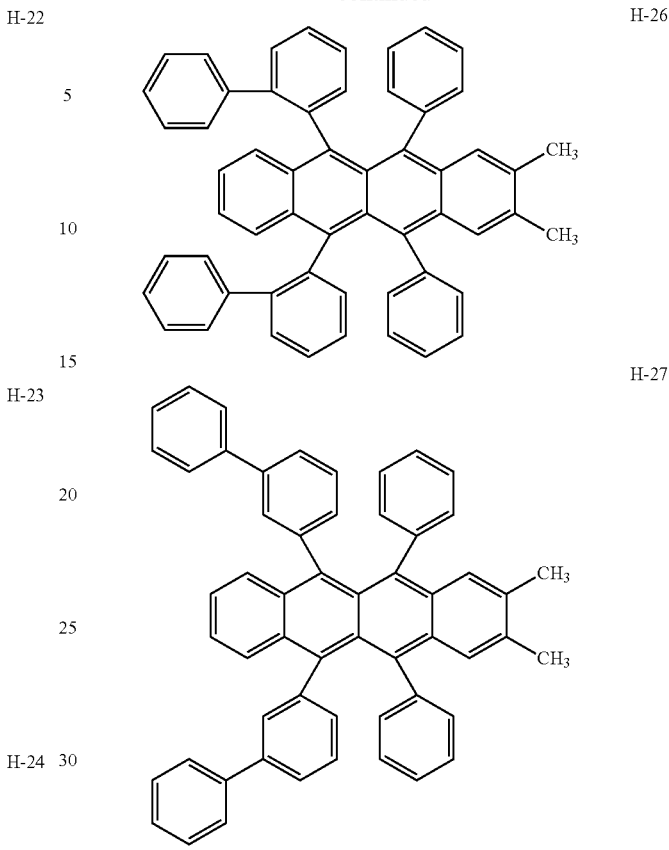

The light emitting layers 33a and 33b including such a light emitting material and host material preferably contain the light emitting material in an amount (doping amount) of 0.01 to 10 wt %, and more preferably in an amount of 0.1 to 5 wt %. When the light emitting material is contained therein in such a range, the light emission efficiency can be optimized.

Moreover, the average thickness of the light emitting layers 33a and 33b is preferably about 1 to 60 nm, and more preferably about 3 to 50 nm, but is not particularly limited thereto.

Electron Transporting Layer

The electron transporting layer 34 has a function for transporting electrons to the light emitting layers 33a and 33b, the electrons being injected from the cathode 37 via the electron injecting layer 35.

Examples of the component material (electron transporting material) of the electron transporting layer 34 include phenanthroline derivatives such as 2,9-dimethyl-4,7-diphenyl-1,10-phenanthroline (BCP), quinoline derivatives such as an organic metal complex, e.g., tris(8-quinolinolato) aluminum (Alq3), that has 8-quinolinol or a derivative thereof as a ligand, azaindolizine derivatives, oxadiazole derivatives, perylene derivatives, pyridine derivatives, pyrimidine derivatives, quinoxaline derivatives, diphenylquinone derivatives, and nitro-substituted fluorene derivatives. These materials can be used alone or in a combination of two or more.

Moreover, in the case where two or more electron transporting materials as described above are used in combination, the electron transporting layer 34 may be constituted by mixed materials in which two or more electron transporting materials are mixed or may be configured by laminating a plurality of layers that are constituted by different electron transporting materials.

In particular, in the case where a tetracene derivative is used in the light emitting layers 33a and 33b as the host material, it is preferable that the electron transporting layer 34 contains an azaindolizine derivative. It is more preferable to use an azaindolizine derivative having an anthracene skeleton in the molecule. Electrons can be efficiently transferred from the anthracene skeleton in the azaindolizine derivative molecule to the host material.

Examples of the azaindolizine derivative can include compounds represented by the following chemical formulae ETL-A1 to ETL-A24, ETL-B1 to ETL-B12, and ETL-C1 to ETL-C20.

Chemical Formula 10

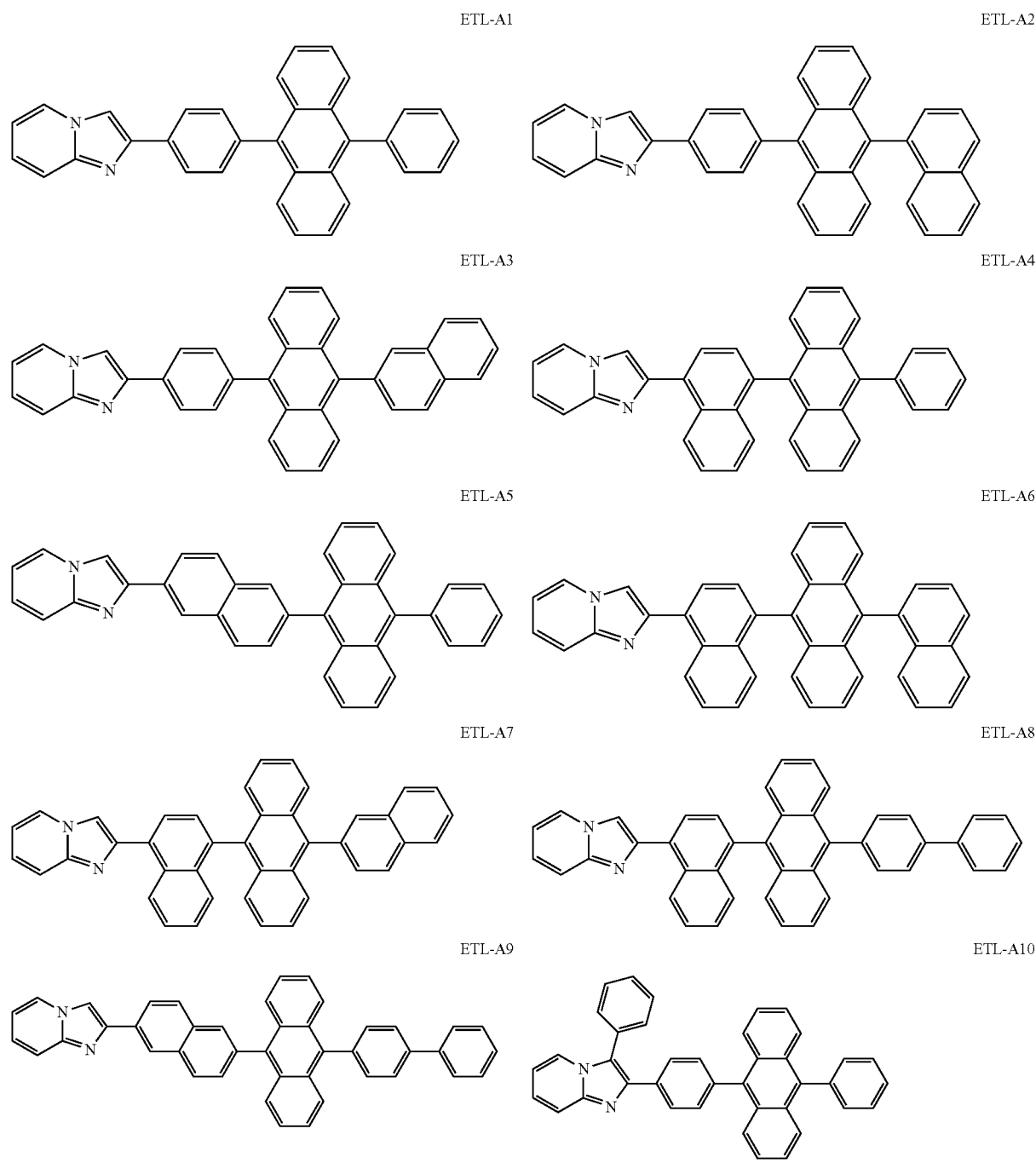

-continued
ETL-A11
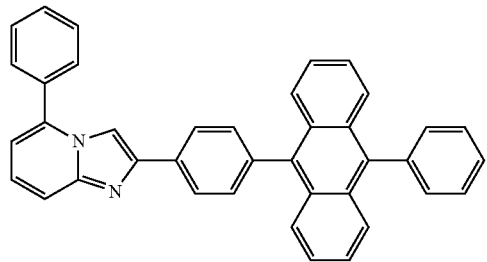
ETL-A12
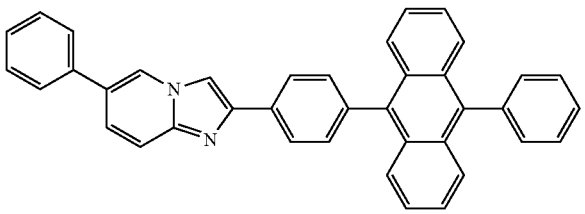
ETL-A13
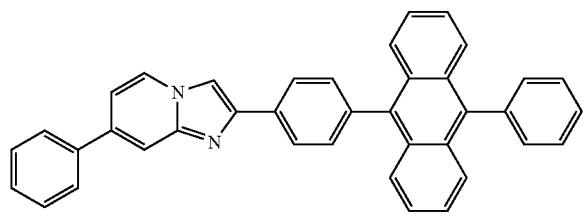
ETL-A14
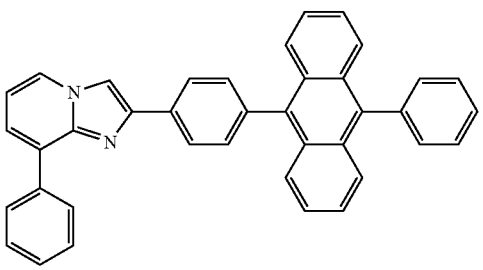
ETL-A15
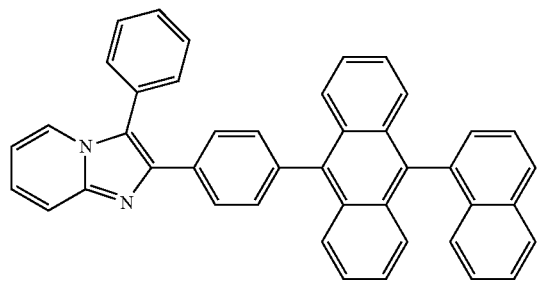
ETL-A16
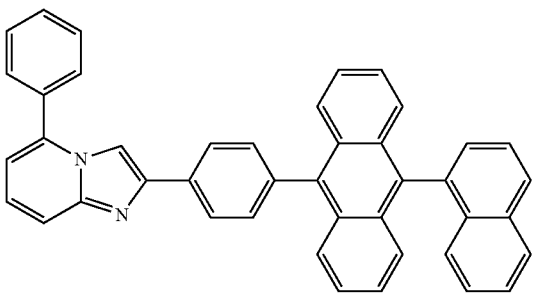
ETL-A17
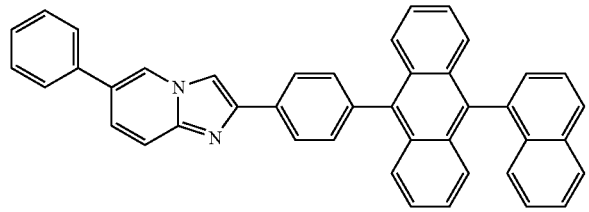
ETL-A18
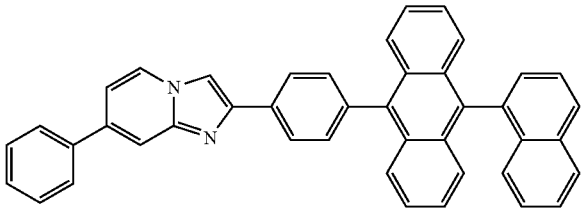
ETL-A19
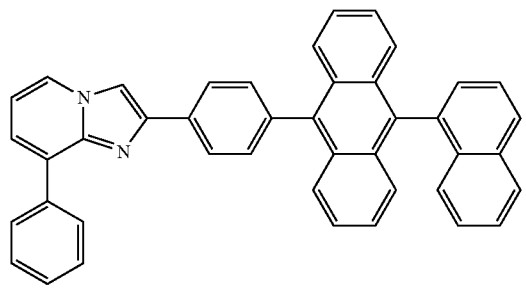
ETL-A20
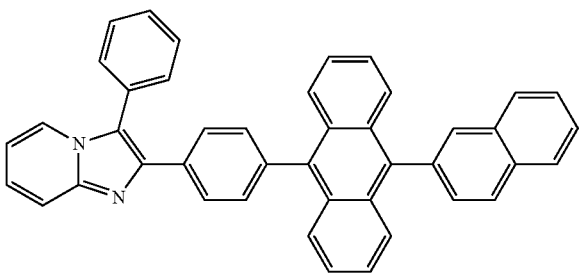

ETL-A21
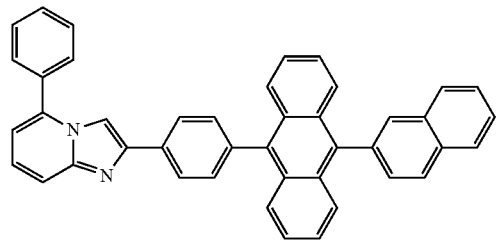
ETL-A22
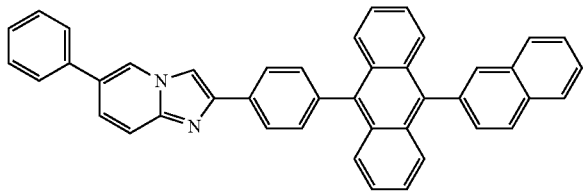
ETL-A23
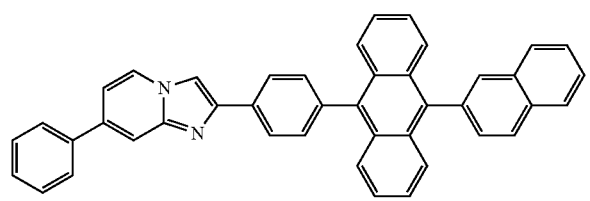
ETL-A24
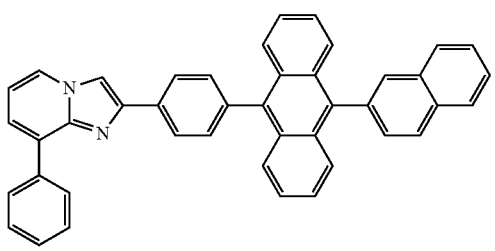
Chemical Formula 11
ETL-B1
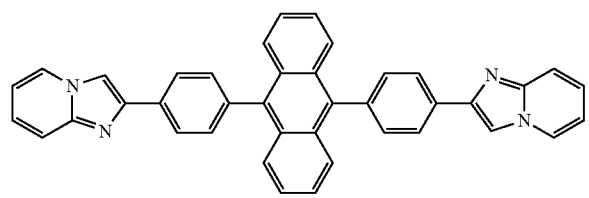
ETL-B2
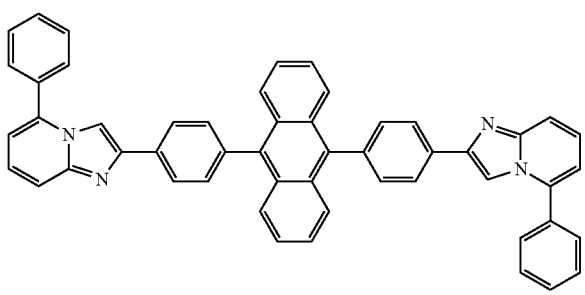
ETL-B3
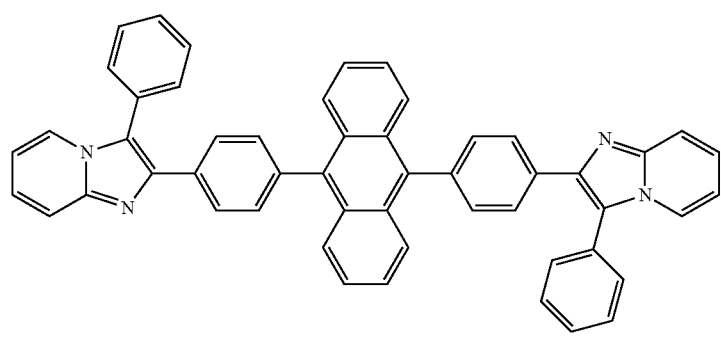
ETL-B4
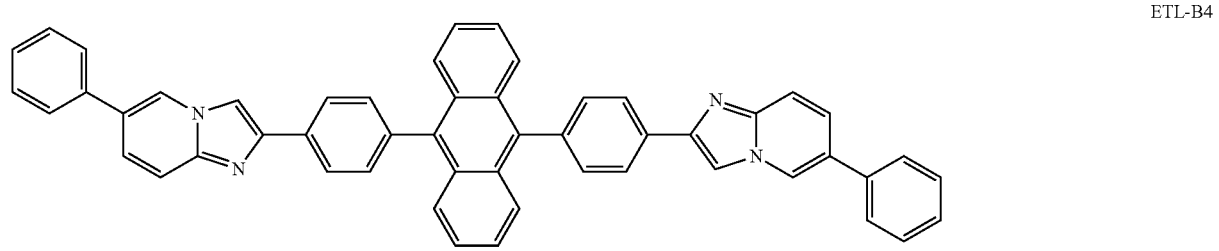

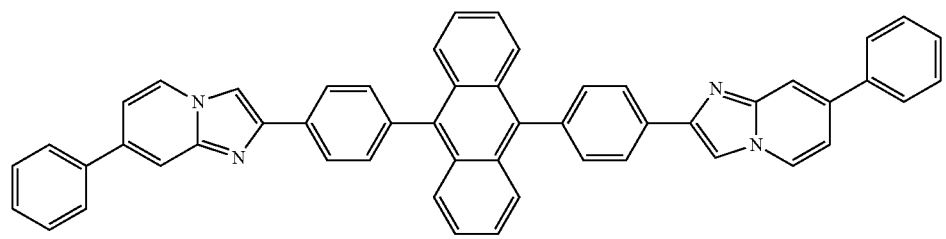
ETL-B5
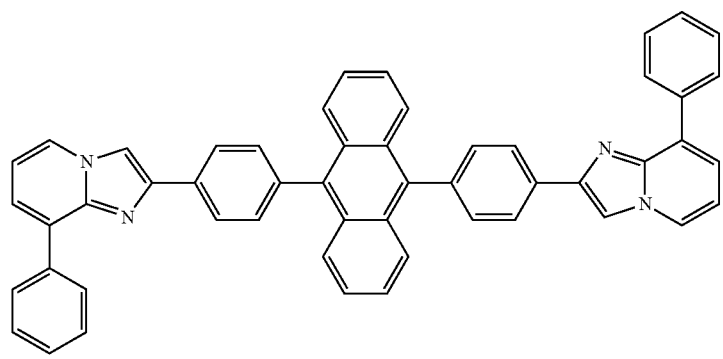
ETL-B6
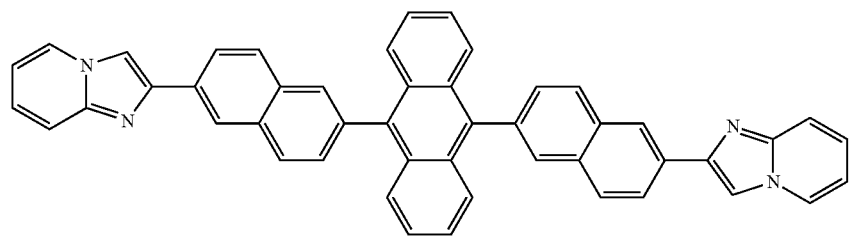
ETL-B7
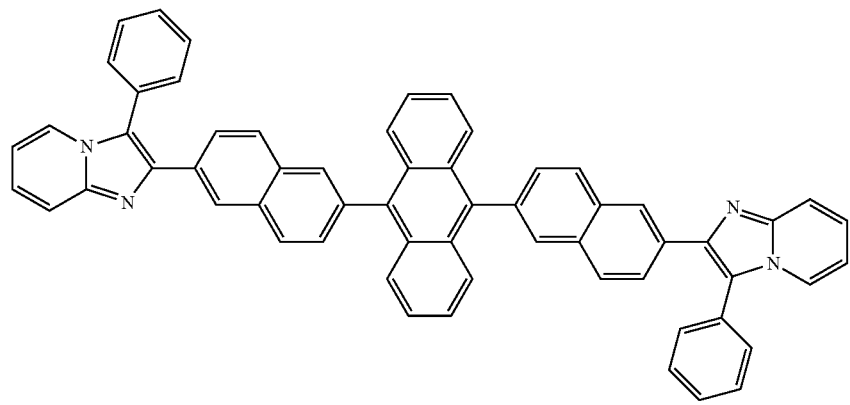
ETL-B8

-continued
ETL-B9
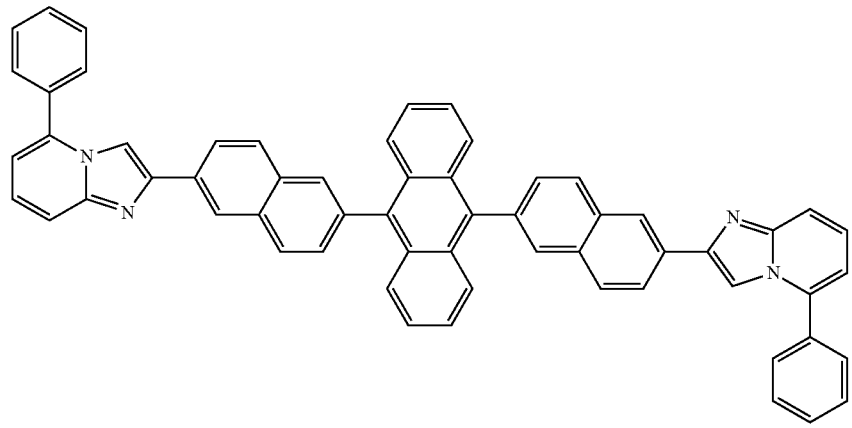
ETL-B10
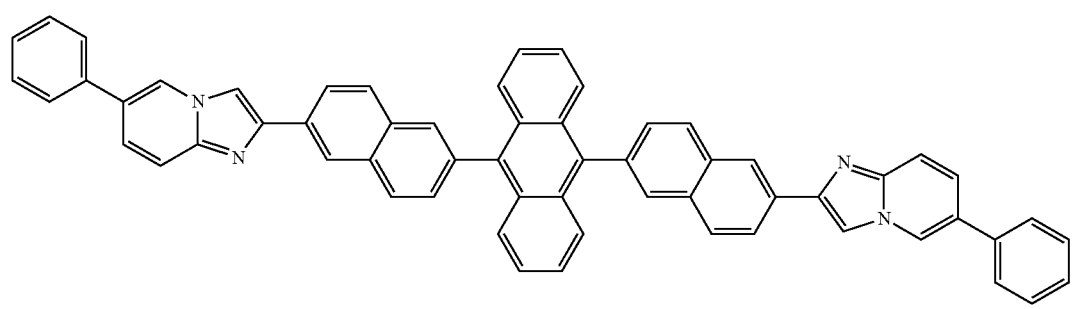
ETL-B11
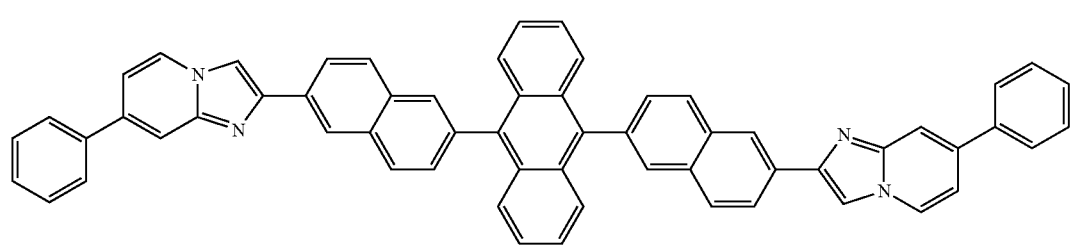
ETL-B12
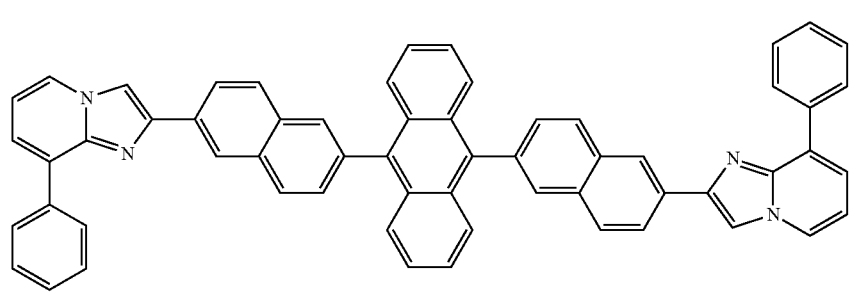
Chemical Formula 12
ETL-C1
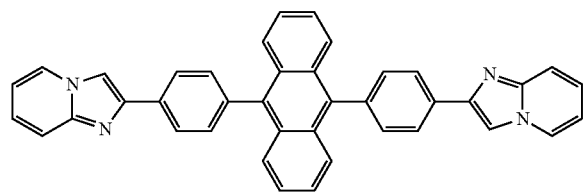
ETL-C2
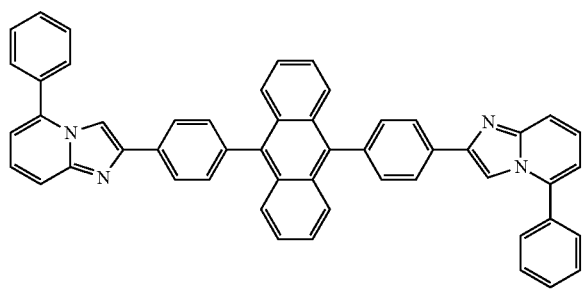

-continued
ETL-C3
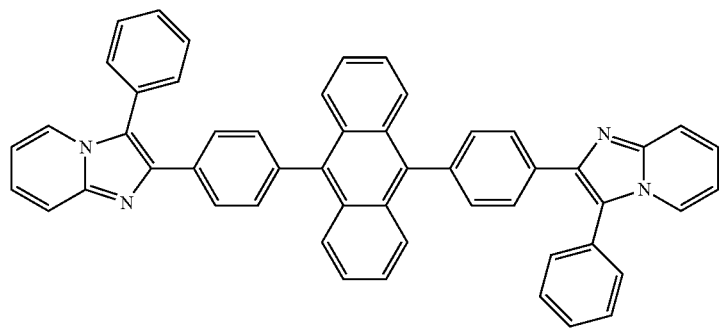
ETL-C4
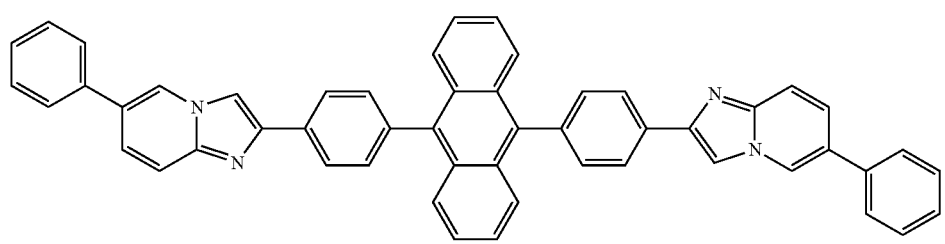
ETL-C5 ETL-C6
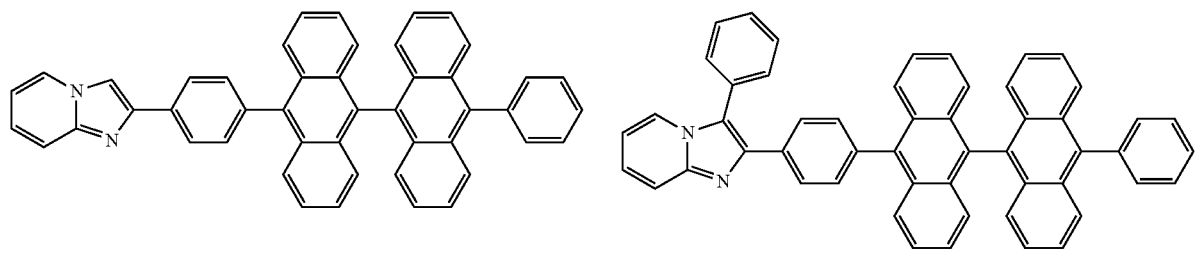
ETL-C7 ETL-C8
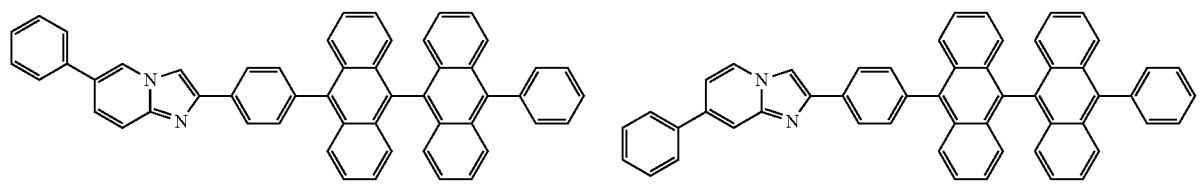
ETL-C9 ETL-C10
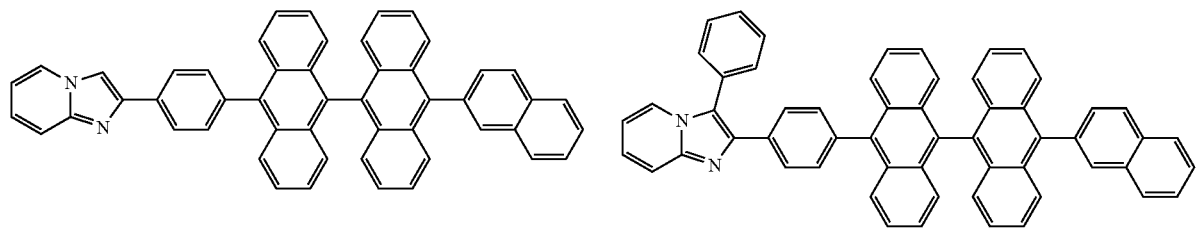
ETL-C11
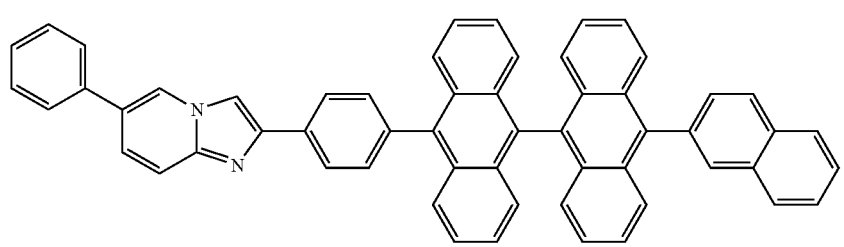

-continued
ETL-C12
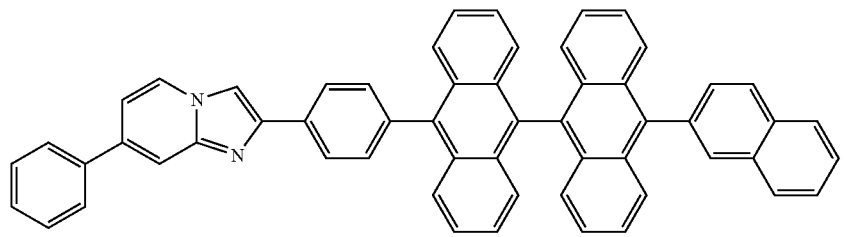
ETL-C13
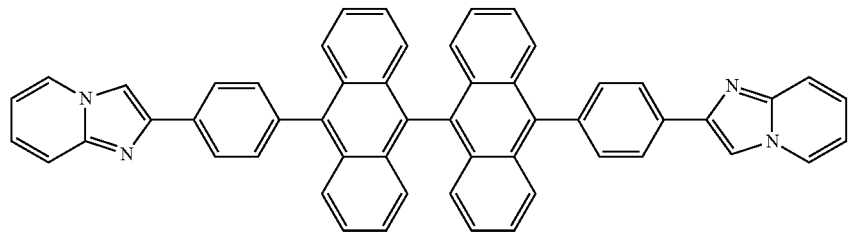
ETL-C14
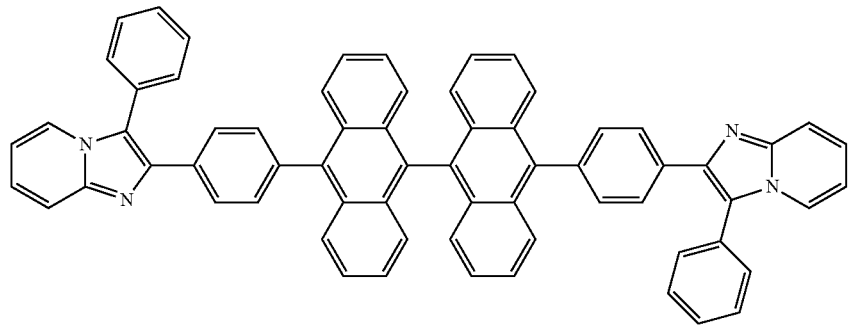
ETL-C15
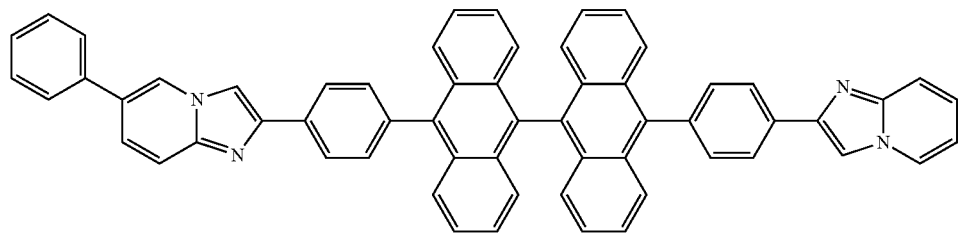
ETL-C16
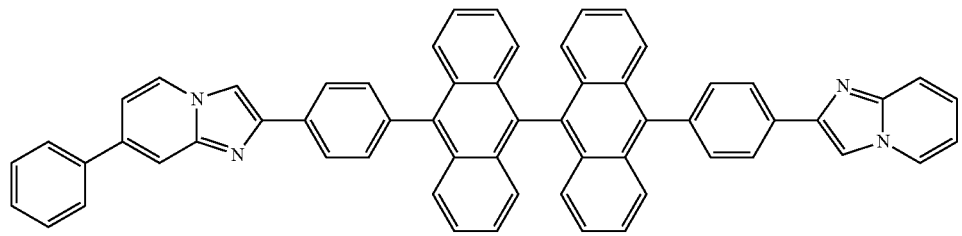
ETL-C17
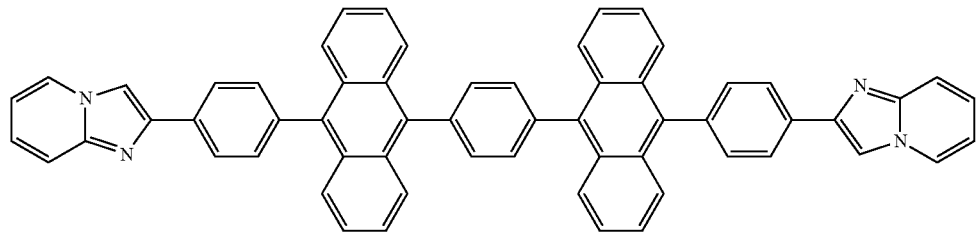

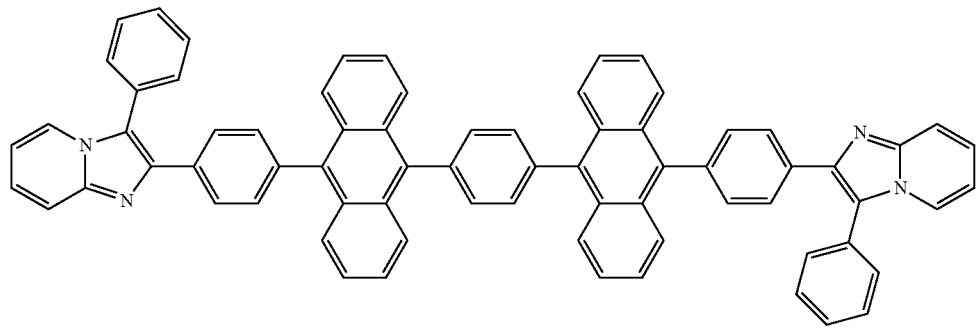

ETL-C18

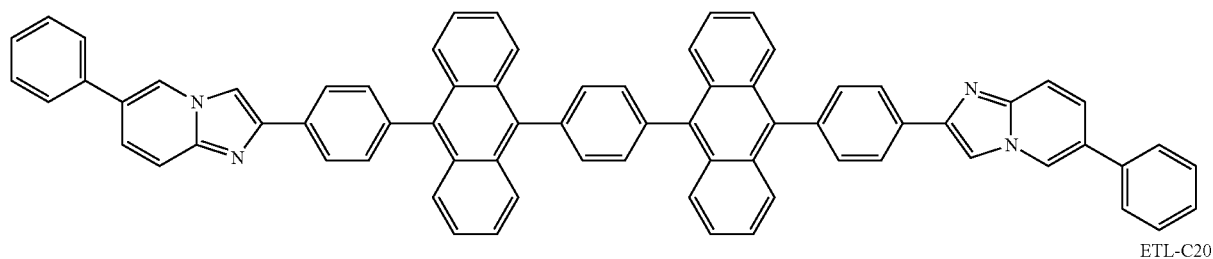

ETL-C19

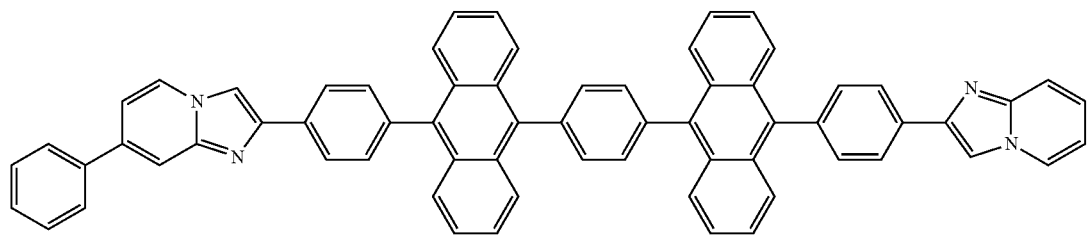

ETL-C20

The average thickness of the electron transporting layer 34 is preferably about 1 to 200 nm, and more preferably about 10 to 100 nm, but is not particularly limited thereto.

It should be noted that a layer provided between the light emitting layer 33a or 33b and the electron injecting layer 35 is not limited to the electron transporting layer 34. A plurality of layers including a layer to which electrons are easily injected from the electron injecting layer 35 and a layer from which electrons are easily transported to the light emitting layer 33a or 33b or a layer for controlling the amount of electrons to be injected to the light emitting layer 33a or 33b may be provided therebetween, for example. In addition, a layer having a function for blocking positive holes that leak from the light emitting layer 33a or 33b to the electron injecting layer 35 side may be included.

Electron Injecting Layer

The electron injecting layer 35 has a function for improving the efficiency of electron injection from the cathode 37.

Examples of the component material (electron injecting material) of this electron injecting layer 35 include various inorganic insulating materials and various inorganic semiconductor materials.

Examples of such inorganic insulating materials include alkali metal chalcogenides (oxides, sulfides, selenides, tellurides), alkaline earth metal chalcogenides, alkali metal halides, and alkaline earth metal halides. These compounds can be used alone or in a combination of two or more. By forming the electron injecting layer (EIL) using these materials as a main material, the electron injecting properties can be further improved. In particular, alkali metal compounds (e.g., alkali metal chalcogenides and alkali metal halides) have a very small work function, and therefore, the first light emitting element 30A and the second light emitting element 30B can be provided with a high luminance by forming the electron injecting layer (EIL) using these compounds.

Examples of the alkali metal chalcogenides include $Li_2O$, LiO, $Na_2S$, $Na_2Se$, and NaO.

Examples of the alkaline earth metal chalcogenides include CaO, BaO, SrO, BeO, BaS, MgO, and CaSe.

Examples of the alkali metal halides include CsF, LiF, NaF, KF, LiCl, KCl, and NaCl.

Examples of the alkaline earth metal halides include $CaF_2$, $BaF_2$, $SrF_2$, $MgF_2$, and $BeF_2$.

Moreover, examples of the inorganic semiconductor materials include oxides, nitrides and oxynitrides that include at least one of Li, Na, Ba, Ca, Sr, Yb, Al, Ga, In, Cd, Mg, Si, Ta, Sb, and Zn. These compounds can be used alone or in a combination of two or more.

The average thickness of the electron injecting layer 35 is preferably about 0.1 to 1000 nm, more preferably about 0.2 to 100 nm, and even more preferably about 0.2 to 50 nm, but is not particularly limited thereto.

It should be noted that this electron injecting layer 35 may be omitted depending on the component material, the thickness, and the like of the cathode 37 and the electron transporting layer 34.

In this embodiment, as a method for forming the functional layers 36a and 36b on the anodes 31, a deposition method is adopted in which the material of each layer is evaporated in a vacuum to form the layer. One example of a method for separately forming the functional layer 36a and the functional layer 36b is a method in which a mask for preventing the formation of one of the functional layers is used while forming the other functional layer. Moreover, the method for forming the functional layers 36a and 36b is not limited to a vapor deposition method such as a deposition method, and a liquid phase growth method may be adopted in which a solution containing the material of each layer is applied, dried, and fired to form the layer. In particular, if a droplet discharging method of the liquid phase growth methods is adopted in which a solution can be discharged from a nozzle of an inkjet head as droplets, a different type of solution can be easily applied for each region partitioned by the partition walls 38 as shown in FIG. 7.

Figure 9:
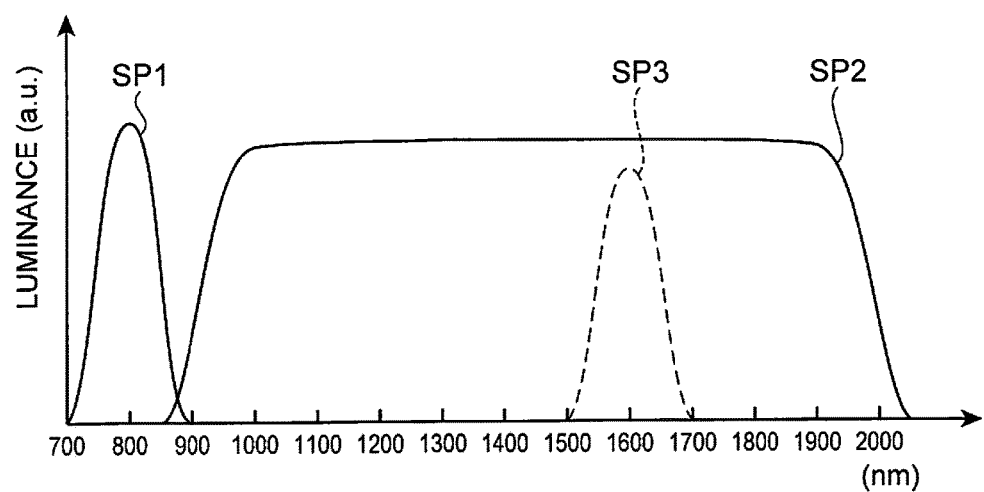
FIG. 9 is a graph illustrating the spectral characteristics of light emitted by a light emitting portion.

Next, the spectral characteristics of infrared light IL emitted by the light emitting portion 110 will be described with reference to FIG. 9. FIG. 9 is a graph illustrating the spectral characteristics of light emitted by a light emitting portion.

Since the first light emitting element 30A in the light emitting portion 110 according to this embodiment has an optical resonance structure as described above, the first light emitting element 30A emits infrared light IL having a spectral distribution SP1 that has a peak wavelength (resonant wavelength) $\lambda 1$ of about 800 nm and is in a wavelength range of 700 to 900 nm as shown in FIG. 9. The second light emitting element 30B emits infrared light IL having a spectral distribution SP2 in a wavelength range of 900 to 2000 nm. The wavelength range of light emitted by the second light emitting element 30B is wider than that of light emitted by the first light emitting element 30A, and the second light emitting element 30B emits light having a peak wavelength $\lambda 2$ of about 1450 nm.

Since the first light emitting element 30A emits light having a peak wavelength (resonant wavelength) $\lambda 1$ of about 800 nm, hemoglobin in blood absorbs a larger amount of the infrared light IL emitted by the first light emitting element 30A than tissue in the human body M absorbs. As a result, reflected light RL reflected by the tissue around the blood vessels in which blood flows increases compared with reflected light RL reflected by the blood vessels, and the amount of the reflected light RL reflected by the blood vessels is different from the amount of the reflected light RL reflected by the tissue around the blood vessels. Therefore, the light receiving element 142 receives the reflected light RL, and thus the output unit 168 can output images of the blood vessels. In other words, from the viewpoint of obtaining the positional information of the blood vessels by utilizing the absorption of light having a specific wavelength by hemoglobin, it is preferable that infrared light IL emitted by the first light emitting element 30A has a peak wavelength $\lambda 1$ in a wavelength range from greater than 700 nm to 900 nm or less. In addition, since infrared light out of the wavelength range of 700 to 900 nm causes noise when being received by the light receiving element 142, it is preferable to emit infrared light in the wavelength range of 700 to 900 nm.

As shown in FIG. 4, the sensor unit 150 includes the variable spectral portion 120 between the light emitting portion 110 and the light receiving portion 140. The second light emitting element 30B in the light emitting portion 110 emits infrared light IL in a wider wavelength range than the wavelength range of infrared light IL emitted by the first light emitting element 30A. The variable spectral portion 120 can selectively transmit infrared light IL having a specific peak wavelength $\lambda 2$ of such wide-band infrared light IL. For example, as shown in FIG. 9, infrared light IL having a spectral distribution SP3 that has a peak wavelength $\lambda 2$ of about 1600 nm and is in a wavelength range of 1500 to 1700 nm can be selectively transmitted. A large amount of the infrared light IL having a peak wavelength $\lambda 2$ of about 1600 nm is absorbed by glucose. Accordingly, when reflected light RL having a peak wavelength $\lambda 2$ of 1600 nm is received by the light receiving element 142, the sensor unit 150 can specify (analyze) the content of glucose, which is a specific component in blood. In particular, the absorbance of glucose has peak wavelengths of 1200 nm, 1600 nm and 2000 nm, and therefore, it is preferable that the second light emitting element 30B can emit infrared light IL in a wavelength range of 900 nm or more to 2000 nm or less from the viewpoint of specifying (analyzing) the content accurately.

Figure 10A:
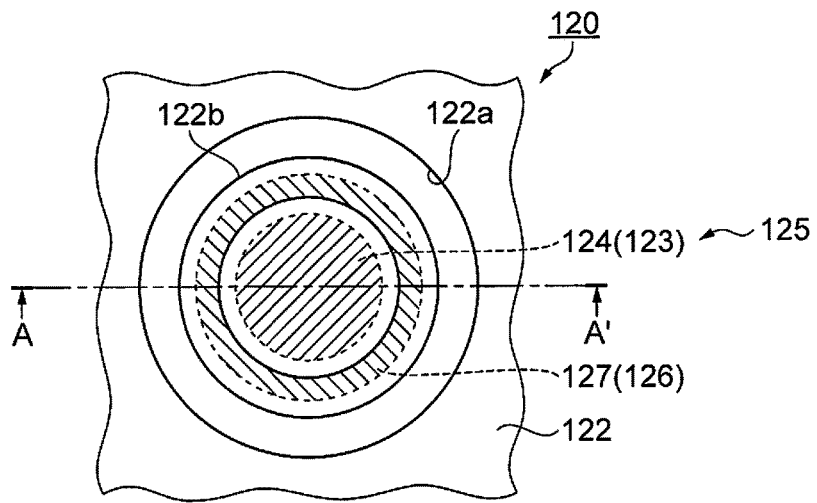
FIGS. 10A to 10C are schematic diagrams illustrating a configuration and operation of a variable spectral portion.
Figure 10B:
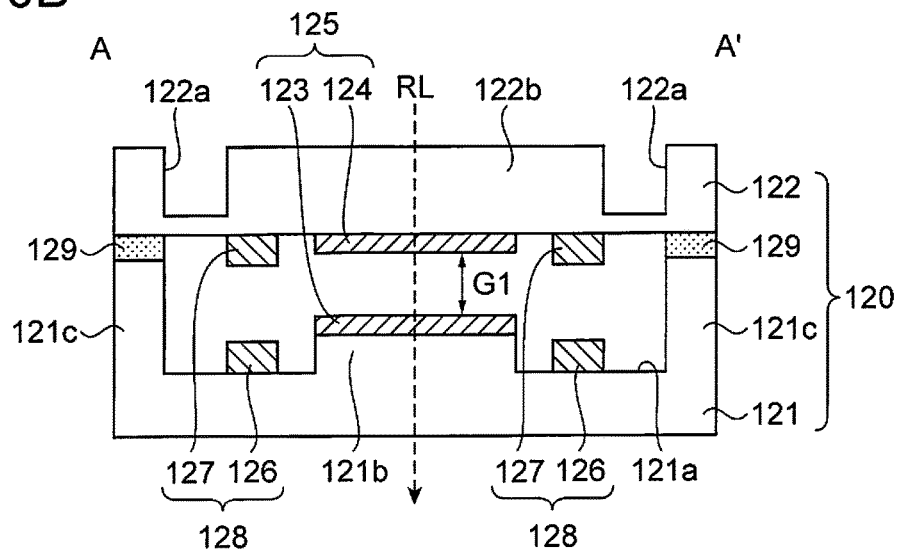
Figure 10C:
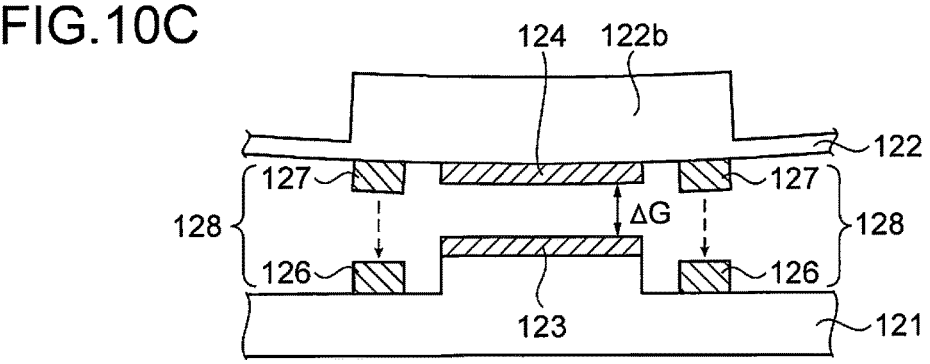

Next, the configuration of the variable spectral portion 120 will be described with reference to FIGS. 10A to 10C. FIGS. 10A to 10C are schematic diagrams illustrating a configuration and operation of a variable spectral portion.

As shown in FIGS. 10A and 10B, the variable spectral portion 120 includes the fixed substrate 121 and the movable substrate 122 disposed so as to be opposed to the fixed substrate 121. A projecting portion 121b is formed on a surface 121a of the fixed substrate 121 on a side opposed to the movable substrate 122. A first optical film 123 is provided on the projecting portion 121b. The projecting portion 121b and the first optical film 123 have a circular shape in a plan view. On the other hand, the movable substrate 122 is provided with a recessed portion (groove) 122a having an annular shape (ring shape) in a plan view. The recessed portion (groove) 122a forms a movable portion 122b having a circular shape in a plan view on the movable substrate 122. A second optical film 124 is formed at a position opposed to the first optical film 123 on the movable portion 122b on the fixed substrate 121 side. The second optical film 124 has a circular shape in a plan view similarly to the first optical film 123. An annular (ring-shaped) first electrode 126 is formed on the surface 121a of the fixed substrate 121 so as to surround the first optical film 123 (projecting portion 121b). Similarly, an annular (ring-shaped) second electrode 127 is formed on the movable portion 122b of the movable substrate 122 so as to surround the second optical film 124.

Light transmissive substrates made of soda glass, quartz, or the like are used as the fixed substrate 121 and the movable substrate 122, and the projecting portion 121b, a supporting portion 121c, the recessed portion (groove) 122a, that is, the movable portion 122b, are formed by etching the substrates. The fixed substrate 121 and the movable substrate 122 are joined together via the supporting portion 121c and a joint portion 129 that are formed around the first electrode 126. By joining the fixed substrate 121 and the movable substrate 122 together, the first optical film 123 and the second optical film 124 are disposed so as to be opposed to each other with a predetermined gap G1 therebetween.

The first optical film 123 and the second optical film 124 disposed so as to be opposed to each other with the predetermined gap G1 therebetween are formed using metal such as Ag, Mg or Ti, an alloy thereof, or an oxide thereof, for example, while the thicknesses of the first optical film 123 and the second optical film 124 are controlled such that they have both light reflecting properties and light transmitting properties. It should be noted that the first optical film 123 and the second optical film 124 may be a single-layer conductive film or a multilayer conductive film. Hereinafter, the first optical film 123 and the second optical film 124 disposed so as to be opposed to each other are referred to as "a pair of optical films 125".

The annular (ring-shaped) first electrode 126 and second electrode 127 formed at positions surrounding the pair of optical films 125 function as an electrostatic actuator 128.

Although not shown in FIGS. 10A to 10C, wiring that is connected to the first electrode 126 is formed in the fixed substrate 121. Similarly, wiring that is connected to the second electrode 127 is formed in the movable substrate 122. The variable spectral portion 120 including the fixed substrate 121 and the movable substrate 122 is electrically connected to the control unit 165 (see FIG. 2). If a DC potential is applied between the first electrode 126 and the second electrode 127, which function as the electrostatic actuator 128, from the control unit 165, it is possible to bring the second electrode 127 closer to the first electrode 126 and to narrow the predetermined gap G1 as shown in FIG. 10C. That is, the optical distance between the pair of optical films 125 is changed by ΔG.

As shown in FIG. 4, the fixed substrate 121 and the movable substrate 122 are provided so as to be opposed to the light transmissive portion 112, which transmits reflected light RL. That is, control of the electrostatic actuator 128 by the control unit 165 enables the optical distance between the pair of optical films 125 to be changed for each light receiving element 142. This makes it possible to change the spectral characteristics of the reflected light RL passing through the pair of optical films 125 corresponding to the amount ΔG of change in the optical distance.

Accordingly, as described above, even if the second light emitting element 30B serving as a light source for spectral analysis has wide-band (broad) spectral characteristics, infrared light (reflected light RL) at 1600 nm that is a wavelength of light that is absorbed by, for example, glucose, which is a specific component in blood, can be selectively guided to the light receiving element 142 by the variable spectral portion 120.

In the portable information terminal 100 including the sensor unit 150, the control unit 165 selects a plurality of first light emitting elements 30A of the light source portion 30 in the light emitting portion 110, and causes the first light emitting elements 30A to emit infrared light IL having a peak wavelength λ1 of about 800 nm. The infrared light IL that is incident on the human body M scatters inside the human body M. A portion of the scattering infrared light IL is guided to the light receiving elements 142 of the light receiving portion 140 as reflected light RL. Images of the blood vessels can be acquired from information (absorbance) of the reflected light RL received by the light receiving elements 142.

Also, the control unit 165 selects a plurality of second light emitting elements 30B of the light source portion 30 in the light emitting portion 110, and causes the second light emitting elements 30B to emit wide-band infrared light IL having a peak wavelength λ2 of about 1450 nm. The infrared light IL that is incident on the human body M scatters inside the human body M. A portion of the scattering infrared light IL is incident on the variable spectral portions 120 as reflected light RL. At this time, the control unit 165 controls the variable spectral portion 120 to narrow the gap G1 between the pair of optical films 125 into a target gap. Thereby, the incident wide-band reflected light RL is guided to the light receiving elements 142 of the light receiving portion 140 as reflected light RL having a peak wavelength λ2 of about 1600 nm. Information (absorbance) of the reflected light RL received by the light receiving elements 142 enables the content of glucose, which is a specific component in blood, to be measured, and the measurement results enable a blood sugar level to be specified (analyzed).

The acquirement of the images of blood vessels and the analysis of a specific component in blood are performed in a staggered manner such that unnecessary light that causes noise is not incident on the light receiving elements 142. When the light source portion 30 emits light, near-infrared light IL may be incident on a portion of the region of the human body M with which the sensor unit 150 is in contact without causing all of the first light emitting elements 30A and all of the second light emitting elements 30B to emit light.

It should be noted that the area of the human body M around which the portable information terminal 100 is worn is not limited to a wrist, and the portable information terminal 100 may also be worn around an arm, an ankle, or a neck from which information of blood vessels and blood can be easily acquired.

With the portable information terminal 100 according to this embodiment, the sensor unit 150 serving as a biological information acquisition device includes the first light emitting elements 30A serving as first infrared light sources, which are used for acquiring positional information of blood vessels and emit infrared light IL having the peak wavelength λ1, and the second light emitting elements 30B serving as second infrared light sources, which are used for spectral analysis and emit infrared light IL having the central wavelength λ2 different from the peak wavelength λ1. The first light emitting element 30A and the second light emitting element 30B are both organic EL elements, and the plurality of first light emitting elements 30A and the plurality of second light emitting elements 30B are disposed on the same surface. Accordingly, a thin, small sensor unit 150 can be realized.

Second Embodiment

Figure 11A:
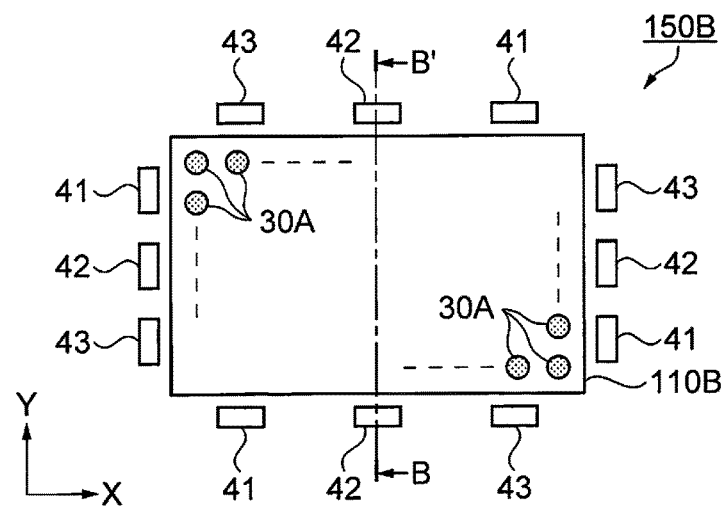
FIG. 11A is a schematic plan view illustrating a configuration of a sensor unit of a second embodiment.

Next, a sensor unit serving as a biological information acquisition device according to a second embodiment will be described with reference to FIGS. 11A and 11B. FIG. 11A is a schematic plan view illustrating a configuration of a sensor unit of the second embodiment, and FIG. 11B is a schematic cross-sectional view taken along line B-B' in FIG. 11A.

The sensor unit according to the second embodiment is different from the sensor unit 150 according to the first embodiment in the configuration of the light source portion 30 of the light emitting portion 110. Accordingly, components that are the same as components of the sensor unit 150 according to the first embodiment are denoted by the same reference numerals, and specific description thereof is omitted.

Figure 11B:
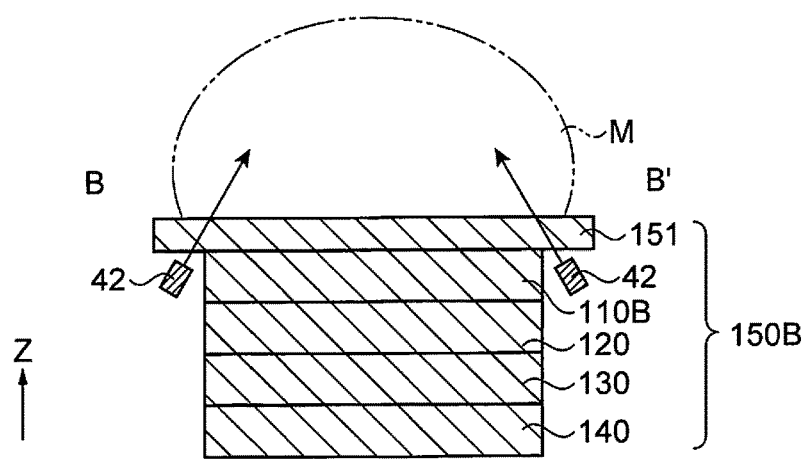
FIG. 11B is a schematic cross-sectional view taken along line B-B' in FIG. 11A.

As shown in FIGS. 11A and 11B, a sensor unit 150B according to this embodiment includes the light receiving portion 140, the light blocking portion 130, the variable spectral portion 120, a light emitting portion 110B, and the protective portion 151 that are stacked in the stated order. In the light emitting portion 110B, the plurality of first light emitting elements 30A are arranged in a matrix in the X direction and the Y direction. Moreover, LED elements 41, 42 and 43 serving as the second infrared light source are disposed around the light emitting portion 110B. As described in the first embodiment, each of the first light emitting elements 30A is an organic EL element in which an optical resonance structure is introduced, and emits infrared light IL having a peak wavelength (resonant wavelength) λ1 of about 800 nm. On the other hand, the LED elements 41, 42 and 43 emit infrared light IL having different peak wavelengths λ2 from one another, and when all of the LED elements 41, 42 and 43 emit light, infrared light IL in a wavelength range of 900 to 2000 nm as shown in FIG. 9 in the first embodiment can be emitted. In other words, one or two LED elements can be selected to emit light, from among the LED elements 41, 42 and 43 capable of emitting infrared light IL having different central wavelengths λ2. That is, it is sufficient to prepare LED elements that are used for spectral analysis and can emit light corresponding to a wavelength of light that is absorbed by a specific component contained in blood. The specific component is not limited to one type, and it is preferable that there are a plurality of types of specific components when the usefulness of the sensor unit 150B is taken into consideration.

As shown in FIG. 11B, the LED elements 41, 42 and 43 are disposed under the protective portion 151. The human body M is irradiated with light that is emitted by the LED elements 41, 42 and 43 and passes through the protective portion 151. In other words, the LED elements 41, 42 and 43 are protected by the protective portion 151. This is a structure in which grime attached to the human body M, such as sweat, does not affect the LED elements 41, 42 and 43.

It should be noted that the number and arrangement of the LED elements 41, 42 and 43, which emit light having the different peak wavelengths λ2, are not limited to those described above.

With the sensor unit 150B according to the second embodiment, the light emitting portion 110B is provided with a plurality of first light emitting elements 30A for acquiring positional information of blood vessels, and therefore, high-definition images of blood vessels can be acquired compared with the first embodiment in which the first light emitting elements 30A and the second light emitting elements 30B are disposed on the same surface.

Third Embodiment

Figure 12:
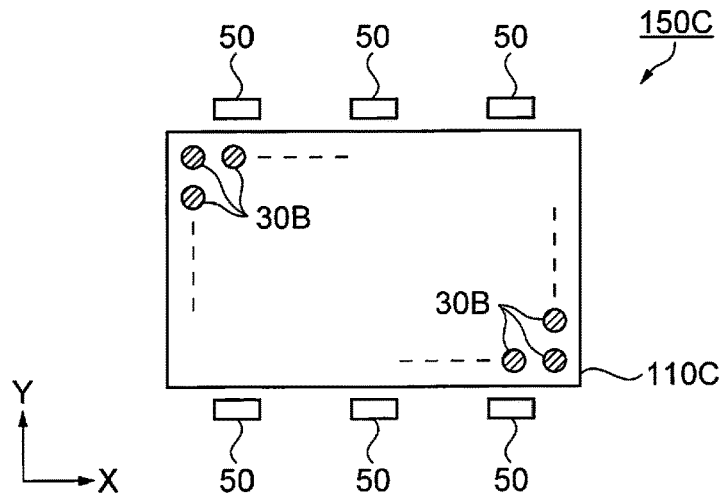
FIG. 12 is a schematic plan view illustrating a configuration of a sensor unit of a third embodiment.

Next, a sensor unit serving as a biological information acquisition device according to a third embodiment will be described with reference to FIG. 12. FIG. 12 is a schematic plan view illustrating a configuration of a sensor unit of a third embodiment.

The sensor unit according to the third embodiment is different from the sensor unit 150B according to the second embodiment in the configurations of the light source portion and LED elements in the light emitting portion 110B. Accordingly, components that are the same as components of the sensor unit 150B according to the second embodiment are denoted by the same reference numerals, and specific description thereof is omitted.

A sensor unit 150C according to this embodiment includes the light receiving portion 140, the light blocking portion 130, the variable spectral portion 120, a light emitting portion 110C, and the protective portion 151 that are stacked in the stated order. As shown in FIG. 12, in the light emitting portion 110C, the plurality of second light emitting elements 30B are arranged in a matrix in the X direction and the Y direction. Moreover, a plurality of LED elements 50 are disposed along the light emitting portion 110C in the X direction. As described in the first embodiment, each of the second light emitting elements 30B is an organic EL element and emits wide-band near-infrared light IL having a peak wavelength λ2 of about 1450 nm. On the other hand, each of the LED elements 50 emits infrared light IL that has a peak wavelength λ1 of about 800 nm and that is in the wavelength range of 700 to 900 nm. It should be noted that the LED elements 50 are disposed under the protective portion 151 and are protected in the same manner as in the second embodiment. Moreover, the number and arrangement of the LED elements 50 are not limited to those described above.

With the sensor unit 150C according to the third embodiment, the light emitting portion 110C is provided with the plurality of second light emitting element 30B for spectral analysis, and therefore, compared with the first embodiment in which the first light emitting elements 30A and the second light emitting elements 30B are disposed on the same surface, a large number of second light emitting elements 30B can be disposed and the luminance of infrared light IL for spectral analysis can be ensured even if the sensor unit 150C is small. Accordingly, a small sensor unit 150C capable of analyzing a specific component in blood with high accuracy can be realized.

The invention is not limited to the forgoing embodiments, and appropriate changes can be made without departing from the gist or the idea of the invention that can be read from the claims or the entire specification. Biological information acquisition devices resulting from such a change and electronic devices in which those biological information acquisition devices are mounted are also included in the technical scope of the invention. Various modified examples other than the foregoing embodiments are conceivable. Hereinafter, modified examples will be described.

Modified Example 1

Figure 13A:
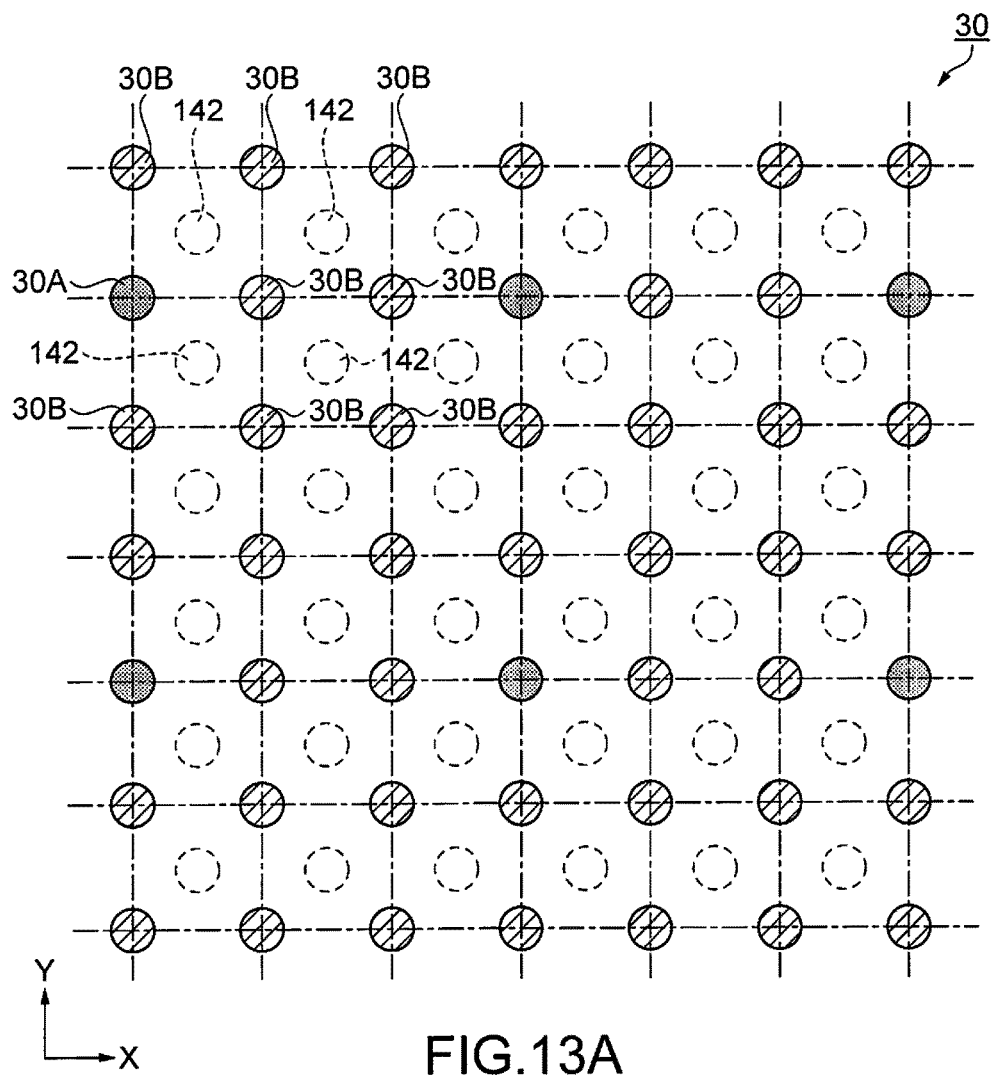
FIGS. 13A to 13C are schematic plan views illustrating an arrangement of first light emitting elements and second light emitting elements of modified examples.
Figure 13B:
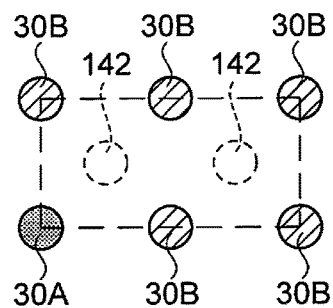
Figure 13C:
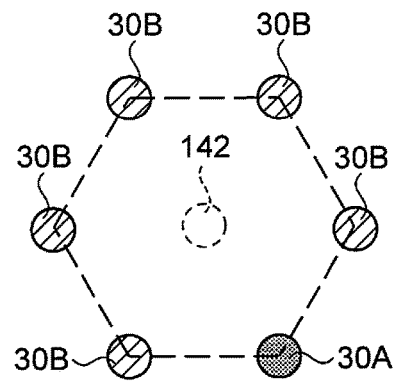

The arrangement of the first light emitting elements 30A and the second light emitting elements 30B in the sensor unit 150 serving as a biological information acquisition device is not limited to that described above. FIGS. 13A to 13C are schematic plan views illustrating an arrangement of first light emitting elements and second light emitting elements of modified examples.

As shown in FIG. 13A, for example, unit pixels are arranged in a matrix, and each unit pixel includes four adjacent light receiving elements 142, and one first light emitting element 30A and eight second light emitting elements 30B that are arranged in a matrix around the four light receiving elements 142 in the same manner. With this configuration, although the first light emitting elements 30A are arranged with larger gaps than those in the first embodiment, the number of second light emitting elements 30B per unit area can be increased, thus making it easy to ensure the luminance of infrared light IL for spectral analysis.

Moreover, the shape of the unit pixel is not limited to a square shape, and may be a rectangular shape including two adjacent light receiving elements 142, and one first light emitting element 30A and five second light emitting elements 30B that are arranged so as to surround the two light receiving elements 142 as shown in FIG. 13B, for example. Furthermore, as shown in FIG. 13C, for example, the unit pixel may have a hexagonal shape including a light receiving element 142 that is arranged at the center, and one first light emitting element 30A and five second light emitting elements 30B that are arranged around the light receiving element 142 as the center.

In all of these modified examples, the number of second light emitting elements 30B is larger than the number of first light emitting elements 30A in order to ensure the luminance of infrared light IL for spectral analysis.

Modified Example 2

Figure 14:
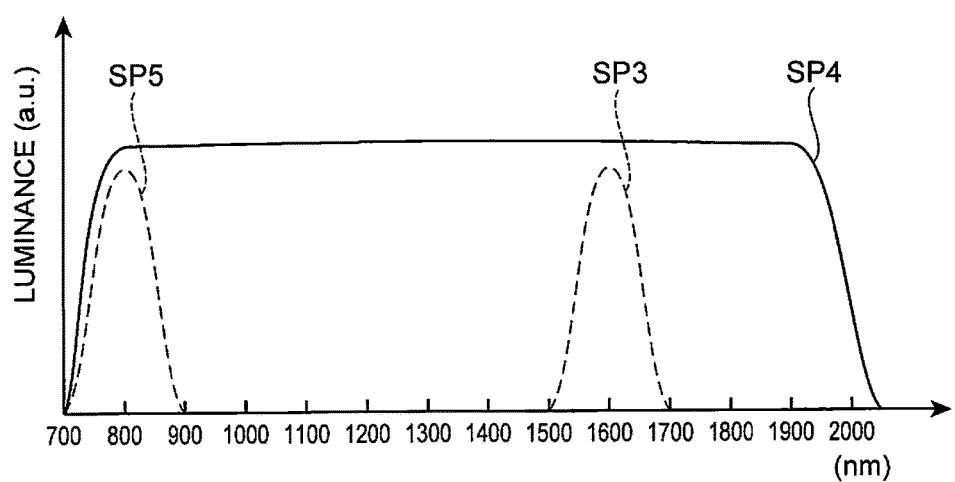
FIG. 14 is a graph illustrating the spectral characteristics of light emitted by a light source portion of a modified example.

The sensor unit 150 serving as a biological information acquisition device is not limited to a sensor unit including both the first infrared light source that emits infrared light IL having a peak wavelength $\lambda 1$ and the second infrared light source that emits infrared light IL having a peak wavelength $\lambda 2$ that is different from the peak wavelength $\lambda 1$. FIG. 14 is a graph illustrating the spectral characteristics of light emitted by a light source portion of a modified example. A plurality of light emitting elements that emit wide-band infrared light IL in a wavelength range of 700 nm or more to 2000 nm or less as shown in FIG. 14 are disposed on the substrate main body 111 and emit light. On the other hand, the variable spectral portion 120 is disposed between the light emitting portion 110 and the protective portion 151. Thus, by varying the spectral distribution of infrared light IL emitted by the light emitting element using the variable spectral portion 120, the human body M is irradiated with the infrared light IL having a spectral distribution SP5 that has a peak wavelength $\lambda 1$ for acquiring positional information of blood vessels of about 800 nm, and the reflected light RL is received by the light receiving elements 142. Also, by varying the spectral distribution of infrared light IL emitted by the light emitting element using the variable spectral portion 120, the human body M may be irradiated with the infrared light IL having the spectral distribution SP3 that has a peak wavelength $\lambda 2$ capable of analyzing a specific component in blood of 1600 nm, for example, and the reflected light RL may be received by the light receiving elements 142. This makes it possible to simplify the configuration of the light source portion 30.

Modified Example 3

The configuration of the variable spectral portion 120 functioning as a variable band pass filter is not limited to that described above. In the case where the sensor unit 150 becomes smaller, the variable spectral portion 120 may be configured to include a pair of the fixed substrate 121 and the movable substrate 122 such that the reflected light RL passing through the plurality of light transmissive portions 112 in the light emitting portion 110 passes through the pair of optical films 125.

Modified Example 4

Although the LED elements 41, 42 and 43 are disposed around the light emitting portion 110B in the second embodiment, a configuration may be adopted in which a plurality of positions of the human body M are irradiated with infrared light that is emitted by one light source and divided by optical fibers. The same applies to the third embodiment.

Modified Example 5

The optical resonance structure of the top emission type first light emitting element 30A is not limited to an optical resonance structure including the reflection layer 21a. For example, the anode 31 may be made of aluminum or an alloy thereof, which has light reflecting properties, and the reflection layer 21a may be omitted. Also in the second light emitting element 30B, if the anode 31 has light reflecting properties, the reflection layer 21b can be omitted.

Modified Example 6

An electronic device in which the sensor unit 150, 150B or 150C is mounted is not limited to the portable information terminal 100. For example, when any of the sensor unit 150, 150B and 150C is mounted in a personal computer, biometric authentication for specifying a user of the personal computer based on images of blood vessels can be performed. In addition, information of a specific component in blood of the user can be acquired.

Also, for example, aspects of the invention can be mounted in a device for measuring blood pressure, blood sugar level, pulsation, pulse waves, cholesterol level, hemoglobin level, blood water level, blood oxygen level, or the like, as a medical device. Moreover, when a coloring agent is simultaneously used, it is possible to measure liver function (detoxification rate), confirm the position of a blood vessel, and confirm a cancer site. Furthermore, increase in findings about specimens makes it possible to determine whether skin cancer is a benign tumor or a malignant tumor (melanoma). Also, a portion or all of the items are collectively determined, it is possible to determine the indices of a skin age and a degree of health of the skin.

The technical idea of the invention is a biological information acquisition device that can noninvasively acquire biological information. The biological information acquisition device includes an infrared light source that emits infrared light in a wavelength range of 700 to 2000 nm, a light receiving portion for infrared light, and a variable spectral portion. The variable spectral portion guides, to the light receiving portion, infrared light that has luminance with which positional information of blood vessels can be acquired and a peak wavelength $\lambda 1$ in a range of greater than 700 nm to 900 nm or less, and infrared light that has luminance with which information of a specific component in blood can be acquired and a peak wavelength $\lambda 2$ in a range of greater than 900 nm to 2000 nm or less, of infrared light emitted by the infrared light source.

The infrared light source may also include a first infrared light source that emits infrared light having a peak wavelength $\lambda 1$ in a range of greater than 700 nm to 900 nm or less, and a second infrared light source that emits infrared light having the peak wavelength $\lambda 2$ in a range of greater than 900 nm to 2000 nm or less.

It is desirable that the biological information acquisition device includes a control unit for controlling the variable spectral portion such that the infrared light having the peak wavelength $\lambda 1$ in a range of greater than 700 nm to 900 nm or less and the infrared light having the peak wavelength $\lambda 2$ in a range of greater than 900 nm to 2000 nm or less are guided to the light receiving portion in different periods of time.

The entire disclosure of Japanese Patent Application No. 2014-171264 filed Aug. 26, 2014 is hereby incorporated herein by reference.

What is claimed is:
1. A biological information acquisition device comprising:
a first infrared light source that emits infrared light having a peak wavelength $\lambda 1$;
a second infrared light source that emits infrared light having a peak wavelength $\lambda 2$ different from the peak wavelength $\lambda 1$;

a light source substrate having a front surface and a back surface, one of the first infrared light source and the second infrared light source being disposed on the front surface of the light source substrate and the other one of the first infrared light source and the second infrared light source being disposed with respect to the light source substrate:

a light receiving portion that receives infrared light emitted by the first infrared light source or the second infrared light source; and a light receiving portion substrate having a front surface and a back surface, the light receiving portion being disposed on the front surface of the light receiving portion substrate, the light source substrate and the light receiving portion substrate being stacked with each other, with the back surface of the light source substrate and the front surface of the light receiving portion substrate facing each other, and the light receiving portion being disposed on a side opposite to a direction in which infrared light is emitted by the first infrared light source or the second infrared light source.

2. The biological information acquisition device according to claim 1,
wherein the peak wavelength $\lambda 1$ is in a range of greater than 700 nm to 900 nm or less.

3. The biological information acquisition device according to claim 1,
wherein the peak wavelength $\lambda 2$ is in a range of greater than 900 nm to 2000 nm or less.

4. The biological information acquisition device according to claim 1,
wherein the first infrared light source is configured to acquire positional information of blood vessels.

5. The biological information acquisition device according to claim 1,
wherein the second infrared light source is configured to acquire an amount of a specific component contained in blood.

6. The biological information acquisition device according to claim 1,
wherein both of the first infrared light source and the second infrared light source are disposed on the front surface of the light source substrate.

7. The biological information acquisition device according to claim 6,
wherein the first infrared light source includes a plurality of the first infrared light sources and the second infrared light source includes a plurality of the second infrared light sources, and the second infrared light sources are larger in number than the first infrared light sources.

8. The biological information acquisition device according to claim 1,
wherein one of the first infrared light source and the second infrared light source is disposed on the front surface of the light source substrate, with the other one of the first infrared light source and the second infrared light source being disposed around the front surface of the light source substrate.

9. The biological information acquisition device according to claim 8,
wherein the second infrared light source includes a plurality of the second infrared light sources, and each of the plurality of second infrared light sources has a different peak wavelength $\lambda 2$.

10. The biological information acquisition device according to claim 9,
wherein the second infrared light sources are LED elements.

11. The biological information acquisition device according to claim 1,
wherein at least one of the first infrared light source and the second infrared light source is an organic electroluminescent element.

12. The biological information acquisition device according to claim 1, comprising:
a variable band pass filter configured to change a spectral distribution of infrared light that is incident on the light receiving portion.

13. The biological information acquisition device according to claim 12, further comprising
a controller configured to control the variable band pass filter such that infrared light having the peak wavelength $\lambda 1$ and infrared light having the peak wavelength $\lambda 2$ are incident on the light receiving portion in different time periods.

14. The biological information acquisition device according to claim 12, further comprising
a controller configured to control the variable band pass filter such that infrared light having peak wavelengths $\lambda 2$ of different values is incident on the light receiving portion in different time periods, wherein the second infrared light source is a wide-band infrared light source that emits light having a wavelength of 900 nm or more to 2000 nm or less.

15. An electronic device comprising the biological information acquisition device according to claim 1.

* * * * *